US010383848B2

(12) United States Patent
North et al.

(10) Patent No.: US 10,383,848 B2
(45) Date of Patent: Aug. 20, 2019

(54) INDOLE-BASED THERAPEUTICS

(71) Applicants: Creighton University, Omaha, NE (US); Colorado State University Research Foundation, Fort Collins, CO (US)

(72) Inventors: Jeffrey North, Omaha, NE (US); Mary C. Jackson, Fort Collins, CO (US)

(73) Assignees: Creighton University, Omaha, NE (US); Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 15/669,289

(22) Filed: Aug. 4, 2017

(65) Prior Publication Data
US 2018/0036283 A1 Feb. 8, 2018

Related U.S. Application Data

(60) Provisional application No. 62/370,931, filed on Aug. 4, 2016.

(51) Int. Cl.
| | | |
|---|---|---|
| *A61K 31/02* | (2006.01) | |
| *A61K 31/166* | (2006.01) | |
| *A61K 31/404* | (2006.01) | |
| *G01N 27/447* | (2006.01) | |

(52) U.S. Cl.
CPC .......... *A61K 31/404* (2013.01); *A61K 31/166* (2013.01); *A61K 31/02* (2013.01); *G01N 27/447* (2013.01)

(58) Field of Classification Search
None
See application file for complete search history.

(56) References Cited

FOREIGN PATENT DOCUMENTS

| WO | WO2014/037900 | * 3/2014 |
| WO | WO2015164482 | * 10/2015 |

OTHER PUBLICATIONS

Székely et al. (Molecular Microbiology, 99(5):831-834, published online Jan. 19, 2016).*
Catherinot et al. (Journal of Cystic Fibrosis, 12: 74-80, 2013).*
Griffith et al. (Am J Respir Crit Care Med 175:367-416, 2007).*
Bodle et al, "Epidemiology of Nontuberculous Mycobacteria in Patients without HIV Infection, New York City," Emerg. Infect. Dis, Mar. 2008, 14:390-396.
Brown et al, "The Structure Activity Relationship of Urea Derivatives as Anti-Tuberculosis Agents," Bioorganic & Medicinal Chemistry, Sep. 2011, 19:5585-5595.
Brown-Elliott et al, "Clinical and Taxonomic Status of Pathogenic Nonpigmented or Late-Pigmenting Rapidly Growing *Mycobacteria*," Clin. Microbiol. Rev, Oct. 2002, 15:716-746.
Brown-Elliott et al., "Antimicrobial Susceptibility Testing, Drug Resistance Mechanisms, and Therapy of Infections with Nontuberculous *Mycobacteria*," Clin. Microbiol Rev, Jul. 2012, 3:545-582.
Bryant et al., "Population-level genomics identifies the emergence and global spread of a human transmissible multidrug-resistant nontuberculous *Mycobacterium*," Science, Nov. 2016, 354:751-757.
Burgos et al, "Treatment of Multidrug-Resistant Tuberculosis in San Francisco: An Outpatient-Based Approach," Clin. Infect. Dis, 2005, 40:968-975.
Chan et al, "Treatment and Outcome Analysis of 205 Patients with Multidrug-resistant Tuberculosis," Am. J. Respir. Crit. Care Med, May 2004, 169:1103-1109.
Chan et al., "Host immune response to rapidly-growing mycobacteria, an emerging cause of chronic lung disease," Am. J. Respir. Cell. Mol. Biol, 2010, 43:387-93.
Disratthakit and Doi, "In Vitro Activities of DC-159a, a Novel Fluoroquinolone, against *Mycobacterium* Species," Antimicrob. Agents Chemother. Jun. 2010, 54:2684-2686.
Dubuisson et al, "In vitro antimicrobial activities of capuramycin analogues against non-tuberculous *Mycobacteria*," J. Antimicrob. Chemother. Dec. 2010, 65:2590-2597.
Espinal et al, "Standard Short-Course Chemotherapy for Drug-Resistant Tuberculosis Treatment Outcomes in 6 Countries," Jama, 2000, 283:2537-2545.
Faria et al, "General Overview on Nontuberculous *Mycobacteria*, Biofilms, and Human Infection," J. Pathog, 2015, 2015: 809014.
Franz et al., "Design, synthesis and evaluation of indole-2-carboxamides with pan anti-*Mycobacterial* activity," Bioorg Med Chem, Jul. 2017, 25: 3746-3755.
Global Tuberculosis Report, World Health Organization. Geneva, 2015, 126 pages.
Gobel et al, "Treatment of 171 Patients with Pulmonary Tuberculosis Resistant to Isoniazid and Rifampinn," Engl. J. Med, 1993, 328:527-532.
Griffith et al, "An Official ATS/IDSA Statement: Diagnosis, Treatment, and Prevention of Nontuberculous *Mycobacterial* Diseases," Am. J. Respir. Crit. Care Med, 2007, 175:367-416.
Grzegorzewicz et al, "Inhibition of Mycolic Acid Transport Across the *Mycobacterium tuberculosis* Plasma Membrane," Nature Chemical Biology, Apr. 2012, 8:334-341.
Hernandez-Garduno et al, "Increasing Incidence of Nontuberculous *Mycobacteria*, Taiwan, 2000-2008," Emerg. Infect. Dis, Jun. 2010, 16:1047-1048.
Ishizaki et al, "Inhibition of the First Step in Synthesis of the Mycobacterial Cell Wall Core, Catalyzed by the GlcNAc-1-phosphate Transferase WecA, by the Novel Caprazamycin Derivative CPZEN-45," J. Biol. Chem, 2013, 288:30309-30319.
Jemberg et al, "Long-term impacts of antibiotic exposure on the human intestinal microbiota," Microbiology, 2010, 156:3216-3223.
Kondreddi et al., "Design, synthesis, and biological evaluation of indole-2-carboxamides: a promising class of antituberculosis agents," J Med Chem, Nov. 2013, 56:8849-59.

(Continued)

*Primary Examiner* — Bong-Sook Baek
(74) *Attorney, Agent, or Firm* — Fish & Richardson P.C.

(57) ABSTRACT

Provided herein are indole-2-carboxamide compounds useful for the treatment of non-tuberculosis bacterial infections. Exemplary compounds provided herein are useful for the treatment of non-tuberculosis mycobacterial infections. Methods for preparing the indole-2-carboxamide compounds are also provided.

8 Claims, 3 Drawing Sheets

(56) References Cited

OTHER PUBLICATIONS

Lai et al, "Increasing incidence of nontuberculous *Mycobacteria*, Taiwan, 2000-2008," Emerg. Infect. Dis, Feb. 2010, 16:294-296.
Leimane et al, "Clinical outcome of individualised treatment of multidrug-resistant tuberculosis in Latvia: a retrospective cohort study," Lancet, Jan. 2005, 365:318-326.
Lerat et al, "In vivo evaluation of antibiotic activity against *Mycobacterium abscessus*," J. Infect. Dis, Mar. 2014, 209:905-912.
Li et al., "Novel Insights into the Mechanism of Inhibition of MmpL3, a Target of Multiple Pharmacophores in *Mycobacterium tuberculosis*," AAC, 2014, 58:6143-23.
Lun et al, "Indoleamides are active against drug-resistant *Mycobacterium tuberculosis*," Nat. Commun, 2013, 4:2907.
Makarov et al, "Benzothiazinones kill *Mycobacterium tuberculosis* by blocking arabinan synthesis," Science, May 2009, 324:801-804.
Manjunatha et al., "The mechanism of action of PA-824: Novel insights from transcriptional profiling," Commun. Integr. Biol, May 2009, 2:215-218.
Marks et al, "Treatment practices, outcomes, and costs of multidrug-resistant and extensively drug-resistant tuberculosis, United States, 2005-2007," Emerg. Infect. Dis, May 2014, 20:812-821.
Marras et al., "Isolation prevalence of pulmonary non-tuberculous *Mycobacteria* in Ontario, 1997 2003," Thorax, Aug. 2007, 62:661-666.
Martin et al, "Resazurin microtiter assay plate testing of *Mycobacterium tuberculosis* susceptibilities to second-line drugs: rapid, simple, and inexpensive method," Antimicrob. Agents Chemother, Nov. 2003, 47:3616-3619.
Mirsaeidi et al, "Nontuberculous mycobacterial disease mortality in the United States, 1999-2010: a population-based comparative study," PLoS One, Mar. 2014, 9:e91879.
Nahid et al, "Official American Thoracic Society/Centers for Disease Control and Prevention/Infectious Diseases Society of America Clinical Practice Guidelines: Treatment of Drug-Susceptible Tuberculosis," Clin. Infect. Dis, Oct. 2016, 63:e147-195.
Nathanson et al, "Multidrug-resistant tuberculosis management in resource-limited settings," Emerg. Infect. Dis, Sep. 2006, 12:1389-1397.
North et al., "Design, synthesis and anti-tuberculosis activity of 1-adamantyl-3-heteroalyl ureas with improved in vitro pharmacokinetic properties," Bioorganic & Medicinal Chemistry, May 2013, 21:2587-2599.
Obregon-Henao et al., "Susceptibility of *Mycobacterium abscessus* to anti-mycobacterial drugs in preclinical models," AAC, Nov. 2015, 59: 6904-12.
Onajole et al, "Preliminary structure-activity relationships and biological evaluation of novel antitubercular indolecarboxamide derivatives against drug-susceptible and drug-resistant *Mycobacterium tuberculosis* strains," Journal of Medicinal Chemistry, May 2013, 56:4093-4103.
Orme and Ordway, "The host response to non-tuberculous mycobacterial infections of current clinical importance," Infect. Immun, Sep. 2014, 82:3516-22.
Rao et al, "Indolcarboxamide is a preclinical candidate for treating multidrug-resistant tuberculosis," Sci. Transl. Med, Dec. 2013, 5:214ra168.
Scherman et al, "Screening a library of 1600 adamantyl ureas for anti-*Mycobacterium tuberculosis* activity in vitro and for better physical chemical properties for bioavailability," Bioorganic & Medicinal Chemistry, May 2012, 20:3255-3262.
Shang et al., Increased virulence of an epidemic strain of *Mycobacterium massiliense* in mice, PLoS One, 2011, 6:e24726.
Stec et al, "Indole-2-carboxamide-based MmpL3 Inhibitors Show Exceptional Antitubercular Activity in an Animal Model of Tuberculosis Infection," J. Med. Chem, Jul. 2016, 59(13):6232-6247.
Tahaoglu et al, "The treatment of multidrug-resistant tuberculosis in Turkey," N. Engl. J. Med, Jul. 2001, 345:170-174.
Thomson et al, "Changing epidemiology of pulmonary nontuberculous *Mycobacteria* infections," Emerg. Infect. Dis, Oct. 2010, 16:1576-1583.

* cited by examiner

INDOLE-BASED THERAPEUTICS

CROSS-REFERENCE TO RELATED APPLICATIONS

This application claims the benefit of U.S. Provisional Application Ser. No. 62/370,931, filed Aug. 4, 2016, the disclosure of which is incorporated herein by reference in its entirety.

FEDERALLY SPONSORED RESEARCH OR DEVELOPMENT

This invention was made with Government support under Grant No. AI116525 awarded by the National Institutes of Health and National Institute of Allergy and Infectious Diseases. The Government has certain rights in the invention.

TECHNICAL FIELD

The present application provides indole-2-carboxamide compounds useful for the treatment of non-tuberculosis bacterial infections.

BACKGROUND

Non-tuberculous mycobacteria (NTM) are opportunistic pathogens, where the prevalence of NTM pulmonary infections in the United States is increasing. Transmission of these pathogens may occur both from environmental sources and from person-to-person. The *Mycobacterium avium* complex (MAC) and *Mycobacterium abscessus* complex (MABSC) are the two species that account for the vast majority (70-95%) of global NTM infections. While MAC is still, overall, the most common cause of NTM infections in the US (accounting for over 70% of NTM pulmonary infections), over the last 10 years, rapidly-growing NTM of the *M. abscessus* complex (including the subspecies *M. abscessus, M. massiliense* and *M. bolletii*) have emerged as important human pathogens globally, causing an increasing number of pulmonary infections among patients with structural lung disease such as chronic obstructive pulmonary disease, bronchiectasis and cystic fibrosis (CF). MABSC species cause serious, life-threatening chronic lung disease, are responsible for disseminated, often fatal, infections following lung transplantation and are associated with a higher fatality rate than any other rapidly growing mycobacteria. Of growing concern is the report that the prevalence of MABSC infections is becoming higher than that of MAC infections in CF patients worldwide, and that MABSC infections tend to target the younger CF population and those with more severe lung disease. Depending on study site, prevalence rates of MABSC infections among children and adult CF patients range from 5% to 48%. MABSC infection in CF patients is particularly problematic as it results in accelerated inflammatory lung damage, can be impossible to treat (with 60-70% treatment failures despite years of combination therapy), and precludes lung transplantation in many US and European centers. MABSC species are indeed not only the most pathogenic rapidly growing mycobacteria, they are also the most antibiotic-resistant NTM. There are many factors that contribute to the drug resistance or drug tolerance of these microorganisms and as a result, the 2007 American Thoracic Society treatment guidelines cite no proven regimens to treat *M. abscessus* pulmonary infections. Current treatment recommendations include multidrug therapy with combinations of intravenous and oral antibiotics accompanied, in some cases, by surgical resection. Furthermore, most likely reflecting a defect in primary lung defense mechanisms, MABSC strains responsible for lung infections tend to co-occur with other pathogens such as *Pseudomonas aeruginosa* and *Staphylococcus aureus*.

SUMMARY

The present application provides, inter alia, a method of treating a non-tuberculosis mycobacterial infection in a subject in need thereof, comprising administering to the subject a therapeutically effective amount of a compound of Formula I:

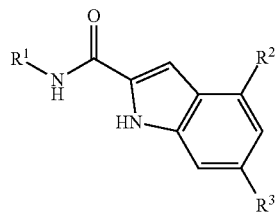

or a pharmaceutically acceptable salt thereof, wherein:

$R^1$ is selected from the group consisting of $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl, wherein the $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl are each optionally substituted by 1, 2, 3, or 4 substituents independently selected from $C_{1-4}$ alkyl and halo; and $R^2$ and $R^3$ are each independently selected from the group consisting of H and $C_{1-4}$ alkyl.

In some embodiments, the non-tuberculosis mycobacterium is selected from *M. avium* complex, *M. abscessus* complex, or a combination thereof. In some embodiments, the non-tuberculosis mycobacterium is selected from the group consisting of *M. abscessus, M. massiliense, M. bolletii, M. chelonae, M. avium, M. xenopi* and *M. smegmatis*. In some embodiments, the non-tuberculosis mycobacterium is selected from the group consisting of *M. xenopi, M. avium, M. smegmatis*, and *M. abscessus*. The method of claim 1 or 2, wherein the non-tuberculosis mycobacterium is *M. abscessus*.

In some embodiments, the non-tuberculosis mycobacterial infection is a hospital acquired mycobacterial infection.

In some embodiments, the subject is further infected with a pathogen selected from *Pseudomonas aeruginosa* and *Staphylococcus aureus*, or a combination thereof.

In some embodiments, the subject has been identified as having a lung disease. In some embodiments, the lung disease is a structural lung disease. In some embodiments, the lung disease is selected from the group consisting of cystic fibrosis, bronchiectasis, emphysema, and chronic obstructive pulmonary disease, and bronchiectasis. In some embodiments, the lung disease is cystic fibrosis. In some embodiments, the subject is a pediatric subject. In some embodiments, the lung disease is pediatric cystic fibrosis.

The present application further provides a method of inhibiting mycolic acid transport in a cell or tissue, comprising contacting the cell or tissue with a compound of Formula I:

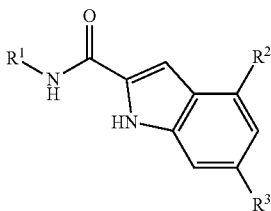

or a pharmaceutically acceptable salt thereof, wherein:

R$^1$ is selected from the group consisting of C$_{5-10}$ cycloalkyl, C$_{6-10}$ aryl, —C$_{1-4}$ alkyl-C$_{5-10}$ cycloalkyl, and —C$_{1-4}$ alkyl-C$_{6-10}$ aryl, wherein the C$_{5-10}$ cycloalkyl, C$_{6-10}$ aryl, —C$_{1-4}$ alkyl-C$_{5-10}$ cycloalkyl, and —C$_{1-4}$ alkyl-C$_{6-10}$ aryl are each optionally substituted by 1, 2, 3, or 4 substituents independently selected from C$_{1-4}$ alkyl and halo; and R$^2$ and R$^3$ are each independently selected from the group consisting of H and C$_{1-4}$ alkyl.

The present application further provides a method of inhibiting translocation of trehalose-monomycolate in a cell or tissue, comprising contacting the cell or tissue with a compound of Formula I:

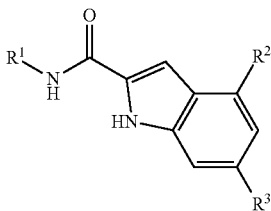

or a pharmaceutically acceptable salt thereof, wherein:

R$^1$ is selected from the group consisting of C$_{5-10}$ cycloalkyl, C$_{6-10}$ aryl, —C$_{1-4}$ alkyl-C$_{5-10}$ cycloalkyl, and —C$_{1-4}$ alkyl-C$_{6-10}$ aryl, wherein the C$_{5-10}$ cycloalkyl, C$_{6-10}$ aryl, —C$_{1-4}$ alkyl-C$_{5-10}$ cycloalkyl, and —C$_{1-4}$ alkyl-C$_{6-10}$ aryl are each optionally substituted by 1, 2, 3, or 4 substituents independently selected from C$_{1-4}$ alkyl and halo; and R$^2$ and R$^3$ are each independently selected from the group consisting of H and C$_{1-4}$ alkyl.

The present application further provides a method of inhibiting mycobacterium membrane protein large 3 (MmpL3) in a cell or tissue, comprising contacting the cell or tissue with a compound of Formula I:

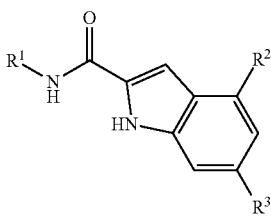

or a pharmaceutically acceptable salt thereof, wherein:

R$^1$ is selected from the group consisting of C$_{5-10}$ cycloalkyl, C$_{6-10}$ aryl, —C$_{1-4}$ alkyl-C$_{5-10}$ cycloalkyl, and —C$_{1-4}$ alkyl-C$_{6-10}$ aryl, wherein the C$_{5-10}$ cycloalkyl, C$_{6-10}$ aryl, —C$_{1-4}$ alkyl-C$_{5-10}$ cycloalkyl, and —C$_{1-4}$ alkyl-C$_{6-10}$ aryl are each optionally substituted by 1, 2, 3, or 4 substituents independently selected from C$_{1-4}$ alkyl and halo; and R$^2$ and R$^3$ are each independently selected from the group consisting of H and C$_{1-4}$ alkyl.

The present application further provides a method of inhibiting mycolic acid transport in a subject, comprising administering to the subject a compound of Formula I:

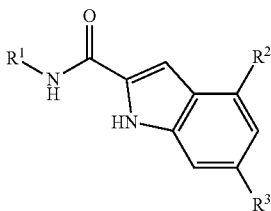

or a pharmaceutically acceptable salt thereof, wherein:

R$^1$ is selected from the group consisting of C$_{5-10}$ cycloalkyl, C$_{6-10}$ aryl, —C$_{1-4}$ alkyl-C$_{5-10}$ cycloalkyl, and —C$_{1-4}$ alkyl-C$_{6-10}$ aryl, wherein the C$_{5-10}$ cycloalkyl, C$_{6-10}$ aryl, —C$_{1-4}$ alkyl-C$_{5-10}$ cycloalkyl, and —C$_{1-4}$ alkyl-C$_{6-10}$ aryl are each optionally substituted by 1, 2, 3, or 4 substituents independently selected from C$_{1-4}$ alkyl and halo; and R$^2$ and R$^3$ are each independently selected from the group consisting of H and C$_{1-4}$ alkyl.

The present application further provides a method of inhibiting translocation of trehalose-monomycolate in a subject, comprising administering to the subject a compound of Formula I:

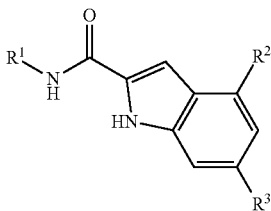

or a pharmaceutically acceptable salt thereof, wherein:

R$^1$ is selected from the group consisting of C$_{5-10}$ cycloalkyl, C$_{6-10}$ aryl, —C$_{1-4}$ alkyl-C$_{5-10}$ cycloalkyl, and —C$_{1-4}$ alkyl-C$_{6-10}$ aryl, wherein the C$_{5-10}$ cycloalkyl, C$_{6-10}$ aryl, —C$_{1-4}$ alkyl-C$_{5-10}$ cycloalkyl, and —C$_{1-4}$ alkyl-C$_{6-10}$ aryl are each optionally substituted by 1, 2, 3, or 4 substituents independently selected from C$_{1-4}$ alkyl and halo; and R$^2$ and R$^3$ are each independently selected from the group consisting of H and C$_{1-4}$ alkyl.

The present application further provides a method of inhibiting mycobacterium membrane protein large 3 (MmpL3) in a subject, comprising administering to the subject a compound of Formula I:

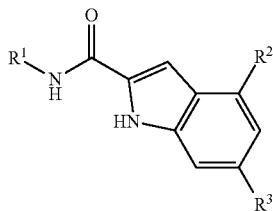

or a pharmaceutically acceptable salt thereof, wherein:

$R^1$ is selected from the group consisting of $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl, wherein the $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl are each optionally substituted by 1, 2, 3, or 4 substituents independently selected from $C_{1-4}$ alkyl and halo; and $R^2$ and $R^3$ are each independently selected from the group consisting of H and $C_{1-4}$ alkyl.

In some embodiments, $R^1$ is selected the group consisting of $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl, wherein the $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl are each optionally substituted by 1, 2, 3, or 4 substituents independently selected from $C_{1-4}$ alkyl and halo. In some embodiments, $R^1$ is selected from the group consisting of $C_{5-10}$ cycloalkyl, —$C_{1-4}$ alkyl-$C_{5-10}$ cycloalkyl, and —$C_{1-4}$ alkyl-$C_{6-10}$ aryl, wherein the $C_{5-10}$ cycloalkyl, —$C_{1-4}$ alkyl-$C_{5-10}$ cycloalkyl, and —$C_{1-4}$ alkyl-$C_{6-10}$ aryl are each optionally substituted by 1, 2, 3, or 4 substituents independently selected from $C_{1-4}$ alkyl and halo. In some embodiments, $R^1$ is selected from the group consisting of $C_{5-10}$ cycloalkyl, —$C_{1-4}$ alkyl-$C_{5-10}$ cycloalkyl, and —$C_{1-4}$ alkyl-phenyl, wherein the $C_{5-10}$ cycloalkyl, —$C_{1-4}$ alkyl-$C_{5-10}$ cycloalkyl, and —$C_{1-4}$ alkyl-phenyl are each optionally substituted by 1, 2, or 3 substituents independently selected from $C_{1-4}$ alkyl and halo. In some embodiments, $R^1$ is selected from the group consisting of $C_{5-10}$ cycloalkyl, —$CH_2$—$C_{5-10}$ cycloalkyl, —$CH(CH_3)$—$C_{5-10}$ cycloalkyl, and —$CH_2$-phenyl, wherein the $C_{5-10}$ cycloalkyl, —$CH_2$—$C_{5-10}$ cycloalkyl, and —$CH_2$-phenyl are each optionally substituted by 1, 2, or 3 substituents independently selected from methyl and chloro. In some embodiments, $R^1$ is selected from the group consisting of monocyclic $C_{5-10}$ cycloalkyl, bicyclic $C_{5-10}$ cycloalkyl, tricyclic $C_{5-10}$ cycloalkyl, —$CH_2$-(tricyclic $C_{5-10}$ cycloalkyl), —$CH(CH_3)$-tricyclic $C_{5-10}$ cycloalkyl, and —$CH_2$-phenyl, wherein the monocyclic $C_{5-10}$ cycloalkyl, bicyclic $C_{5-10}$ cycloalkyl, tricyclic $C_{5-10}$ cycloalkyl, —$CH_2$-(tricyclic $C_{5-10}$ cycloalkyl), —$CH(CH_3)$-tricyclic $C_{5-10}$ cycloalkyl, and —$CH_2$-phenyl, are each optionally substituted by 1, 2, or 3 substituents independently selected from methyl and chloro.

In some embodiments, $R^1$ is selected from the group consisting of:

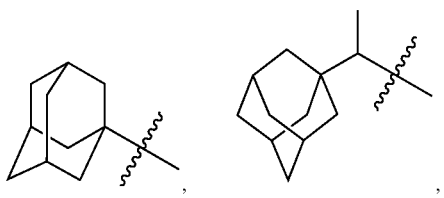

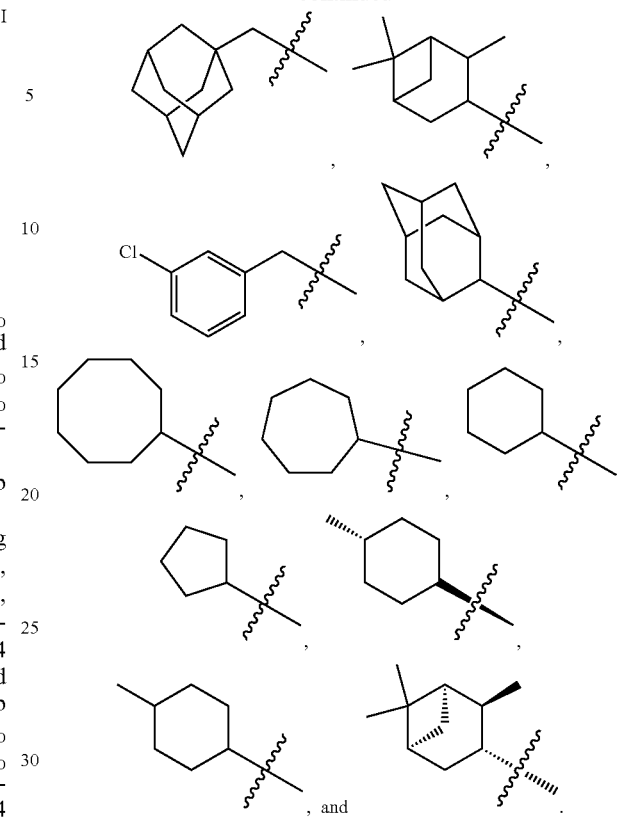

In some embodiments, $R^1$ is selected from the group consisting of:

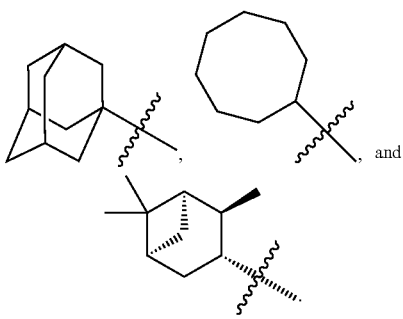

In some embodiments, $R^2$ and $R^3$ are each H. In some embodiments, $R^2$ and $R^3$ are each $C_{1-4}$ alkyl. In some embodiments, $R^2$ and $R^3$ are each methyl.

In some embodiments, the compound of Formula I is selected from the group consisting of:

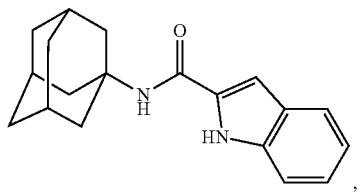

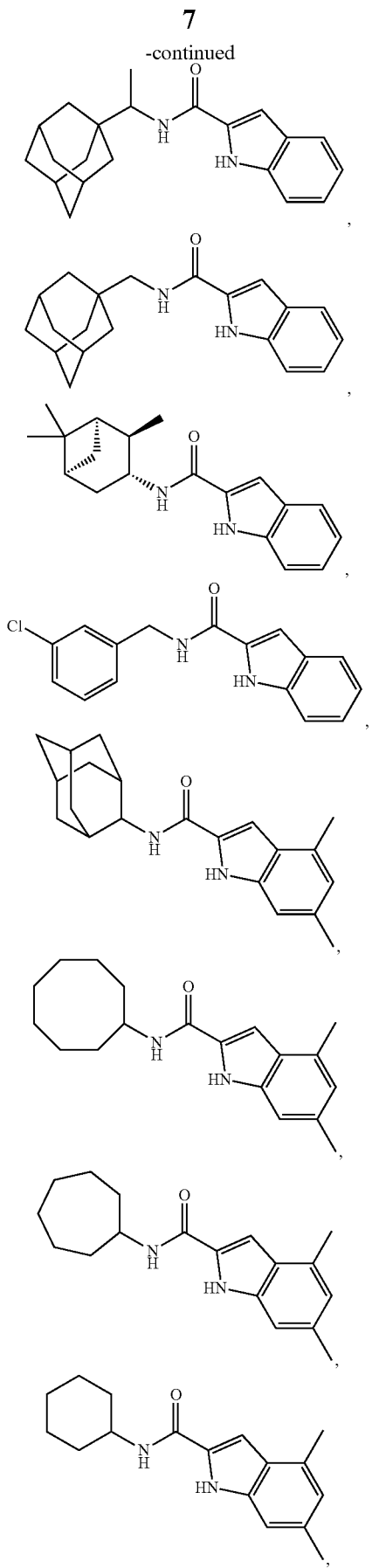
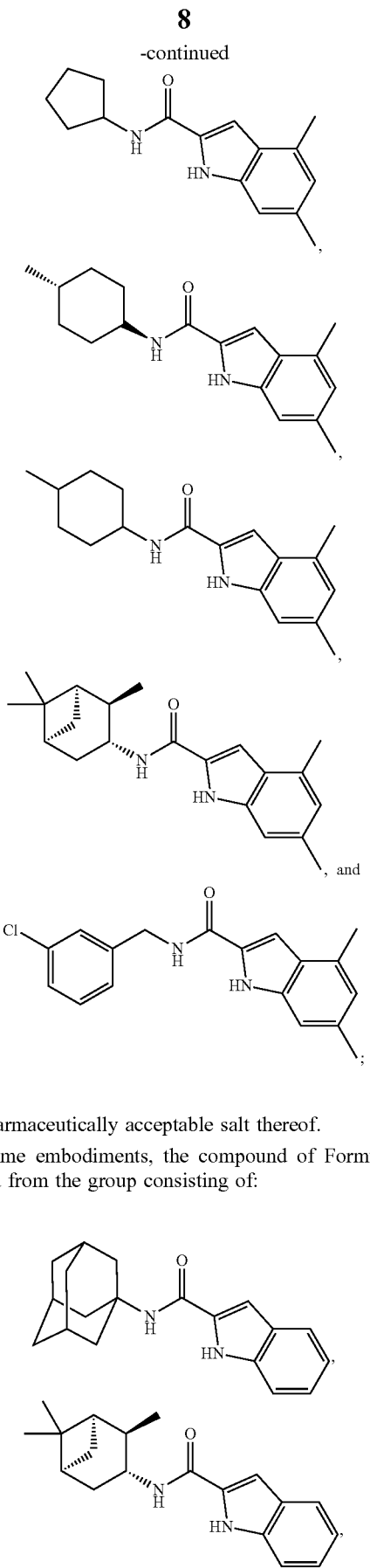
or a pharmaceutically acceptable salt thereof.
In some embodiments, the compound of Formula I is selected from the group consisting of:
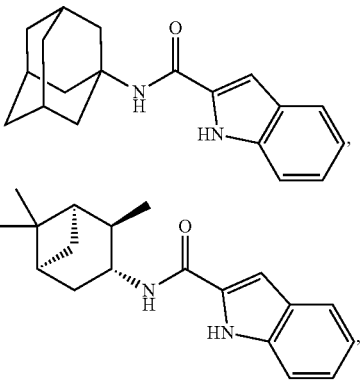

-continued

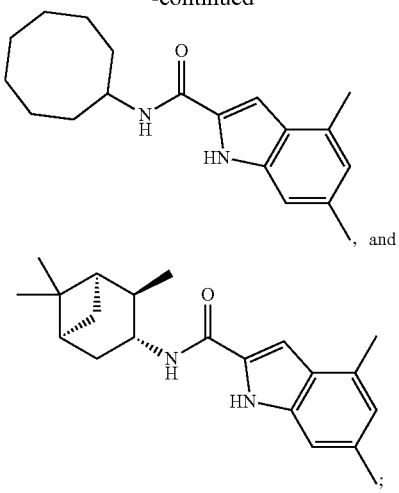

, and or a pharmaceutically acceptable salt thereof.

In some embodiments, the compound of Formula I is selected from the group consisting of

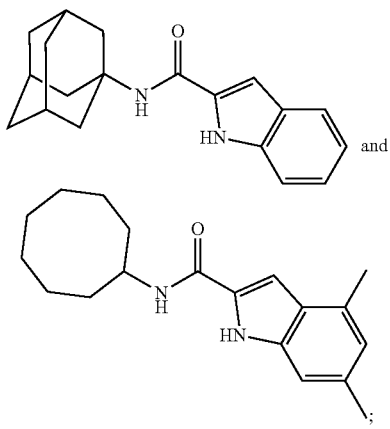

;

or a pharmaceutically acceptable salt thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIG. 1A: Analyses of lipids from untreated and treated cells. The same volume of [$^{14}$C]-labeled lipids from bacterial cells either treated or untreated were analyzed by TLC in the solvent system [CHCl$_3$:CH$_3$OH:H$_2$O, 20:4:0.5] and revealed by phosphorimaging. TMM/TDM ratios, expressed relative to the value measured in the untreated control (arbitrarily set to 1), are presented as histograms. PE, phosphatidylethanolamine; CL, cardiolipin; GPLs, glycopeptidolipids; FM, free mycolates. FIG. 1B: Analyses of cell wall-bound mycolic acid methyl esters (MAMEs) prepared from the same untreated and treated cells as in FIG. 1A. TLC plates were developed thrice in the solvent system [n-hexane:ethyl acetate, 95:5] and revealed by phosphorimaging. The amount of radioactivity incorporated in MAMEs was semi-quantified using a PhosphorImager and the results, expressed as a percentage of the value measured in the untreated control, are presented as histograms.

DETAILED DESCRIPTION

Figure 1A:
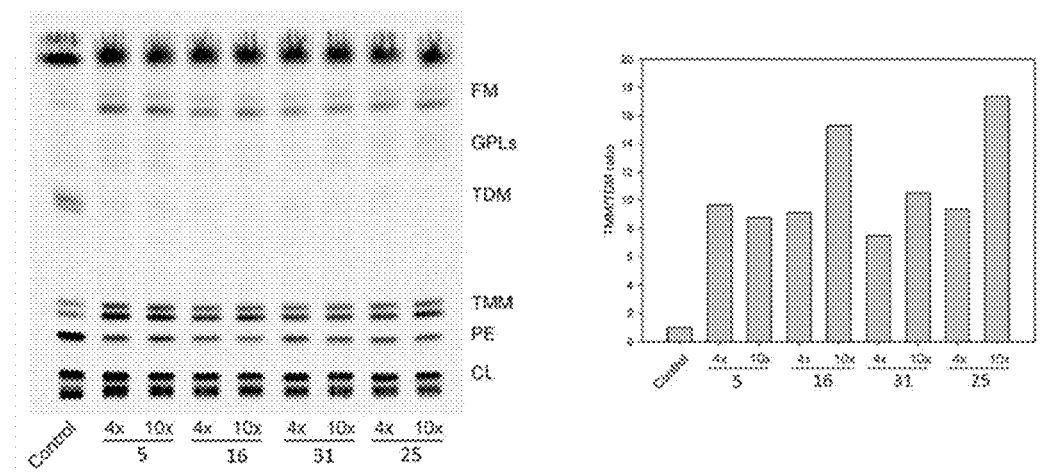
FIGS. 1A-1B show the effect of indolecarboxamides on the transfer of mycolic acids to their cell envelope acceptors. *M. massiliense* strain 1513 were either untreated or treated with compound 5 (4 µg/mL [4×MIC] or 10 µg/mL [10× MIC]), 16 (2 µg/mL [4×MIC] or 5 µg/mL [10×MIC]), 31 (2 µg/mL [4×MIC] or 5 µg/mL [10×MIC]) or 25 (0.5 µg/mL [4×MIC] or 1.25 µg/mL [10×MIC]) and labeled with [1,2-$^{14}$C]acetate as described in Example 34.

Non-tuberculous mycobacteria (NTM) are ubiquitous environmental pathogens that can cause a wide variety of infections, such as: progressive pulmonary disease, skin and soft tissue infections, lymphadenitis, and disseminated disease (see e.g., Brown-Elliott et al, *Clin. Microbiol. Rev.* 2002, 15:716-746; and Faria et al, *J. Pathog.* 2015, 809014). The most common human pathogens are the species *M. avium* complex (MAC) and *M. kansasii*, however other clinically relevant species include the *M. abscessus* complex (MABSC, including the subspecies *M. abscessus*, *M. massiliense* and *M. bolletii*) and *M. fortuitum* (see e.g., Griffith et al, *Am. J. Respir. Crit. Care Med.* 2007, 175:367-416). NTM commonly cause pulmonary disease in older, immunocompromised patients who have underlying lung disease.

The precise frequency of NTM disease is unknown because reporting for NTM is not mandatory in the United States and many other countries (see e.g., Bodle et al, *Emerg. Infect. Dis.* 2008, 14:390-396; and van der Werf et al, *BMC Infect. Dis.* 2014, 14:62). Furthermore, current incidence and prevalence data are likely underestimated due to the indolent nature of NTM pulmonary disease, the most common form of NTM infections. A growing number of studies suggest that the number of NTM infections and mortality rates continue to increase (see e.g., Bodle et al, *Emerg. Infect. Dis.* 2008, 14:390-396; and Thomson et al, Emerg. Infect. Dis. 2010, 16:1576-1583). Growing prevalence of NTM isolates between 1997 (9.1/100,000) and 2003 (14.1/100,000) has been observed in Ontario, Canada (see e.g., Marras et al, *Thorax,* 2007, 62:661-666). More recently, Taiwan has reported increasing incidence of NTM disease, 10.2 cases per 100,000 persons in 2008 compared to 2.7 cases per 100,000 persons in 2000 (see e.g., Hernandez-Garduno et al, *Emerg. Infect. Dis.* 2010, 16:1047-1048; and Lai et al, *Emerg. Infect. Dis.* 2010, 16:294-296). In addition, estimates from 1999 to 2010 suggest the number of immediate NTM-related deaths in the United States rose significantly and are expected to increase over the next few years, given the increasing median age in North America (see e.g., Mirsaeidi et al, *PLoS One,* 2014, 9:e91879). Although NTM are opportunistic pathogens, they represent a matter of significant concern to health practitioners because of increasing incidence and mortality rates. As the number of patients with immune-compromising conditions continues to grow, both opportunistic and primary cases of NTM infection present a significant challenge for current antibiotic therapy.

In contrast to the insidious nature of NTM infections, *M. tuberculosis* is the cause of highly transmittable disease and infects about one-third of the world's population (see e.g., *Global Tuberculosis Report*, World Health Organization: Geneva, 2015). In 2015, tuberculosis (TB) became the leading infectious disease killer in the world and caused illness in approximately 9.6 million people, killing 1.5 million each year (see e.g., *Global Tuberculosis Report*, World Health Organization: Geneva, 2015). The global incidence of multi-drug-resistant tuberculosis (MDR-TB) remains unchanged at 3.3%, causing growing concern for healthcare professionals. MDR-TB is classified as resistant to both rifampicin and isoniazid, two antibiotics used in standard treatment. This form of TB goes largely undetected, as the estimated number of cases of MDR-TB in 2014 was 480,000 people and the number of these patients who were started on appropriate treatment was only about 111,000. Currently, there are few narrow spectrum antimycobacterial antibiotics. The current treatment of NTM recommended by the American Thoracic Society (ATS) and Infectious Diseases Society of America (IDSA) includes regimens of multiple antibiotics, potentially including macrolides, aminoglycosides, fluoroquinolones, oxazolidinones, tigecycline, carbapenems, cephalosporins, sulfonamides, ethambutol, and rifampicin (see e.g., Griffith et al, *Am. J. Respir. Crit. Care Med.* 2007, 175:367-416). Many of these recommendations are made on the basis of preliminary in vitro efficacy studies due to the lack of a standardized animal model. Depending on the organism and site of infection, two to four of these agents are often used in combination for a duration of at least 12 months after the first negative culture. The use of multiple antibiotics for prolonged periods of time is challenging due to common complications such as drug interactions and noncompliance.

Problems surrounding current anti-TB therapy are similar to that of NTM. The treatment of drug-susceptible TB focuses on the same four-antibiotic regimen (isoniazid, rifampicin, ethambutol, and pyrazinamide) introduced more than 40 years ago (see e.g., *Global Tuberculosis Report*, World Health Organization: Geneva, 2015). The therapy typically requires the use of multiple antibiotics and is long in duration; these are both factors contributing to non-compliance and treatment failure, which can lead to the emergence of MDR-TB and extensively drug-resistant tuberculosis (XDR-TB). The treatment of MDR-TB/XDR-TB is more difficult and requires multiple broad-spectrum antibiotics, which exposes patients to complications like *Clostridium difficile* infections and other resistant microorganisms (see e.g., Jernberg et al, *Microbiology,* 2010, 156:3216-3223). Clinical practice guidelines for the treatment of drug-resistant TB are currently under development by the ATS and IDSA (see e.g., Nahid et al, *Clin. Infect. Dis.* 2016, 63:e147-195). Depending on the susceptibilities of particular drug-resistant TB strains, second-line anti-TB drugs are typically used for a duration of 2 years and treatment success rates range from 30 to 80%, underscoring the need for newer anti-mycobacterial drugs and treatment regimens that maximize efficacy and shorten duration of treatment (see e.g., Burgos et al, *Clin. Infect. Dis.* 2005, 40:968-975; Chan et al, *Am. J. Respir. Crit. Care Med.* 2004, 169:1103-1109; Espinal et al, *Jama,* 2000, 283:2537-2545; Gobel et al, *N. Engl. J. Med.* 1993, 328:527-532; Leimane et al, *Lancet,* 2005, 365:318-326; Marks et al, *Emerg. Infect. Dis.* 2014, 20:812-821; Nathanson et al, *Emerg. Infect. Dis.* 2006, 12:1389-1397; and Tahaoglu et al, *N. Engl. J. Med.* 2001, 345:170-174).

Current drugs that are in the pharmaceutical pipeline for mycobacterial infections are largely being used against *M. tuberculosis* and not specifically against NTM. In preclinical and clinical trials, drugs in the pipeline are often studied in combination drug regimens with other broad-spectrum antibiotics. Furthermore, these drugs, including DC-159a (see e.g., Disratthakit et al, *Antimicrob. Agents Chemother.* 2010, 54:2684-2686), SQ-641 (see e.g., Dubuisson et al, *J. Antimicrob. Chemother.* 2010, 65:2590-2597), CPZEN-45 (see e.g., Ishizaki et al, *J. Biol. Chem.* 2013, 288:30309-30319), BTZ043 (see e.g., Makarov et al, *Science,* 2009, 324:801-804), bedaquiline (see e.g., Lerat et al, *J. Infect. Dis.* 2014, 209:905-912), and pretomanid (see e.g., Manjunatha et al, *Commun. Integr. Biol.* 2009, 2:215-218), lack bactericidal activity against many NTM species. The development of narrow-spectrum anti-mycobacterial drugs could revolutionize the treatment of both TB and NTM.

Indole-2-carboxamides (IC) have been reported as novel antitubercular agents with activity against drug-resistant strains and in in vivo efficacy mouse models (see e.g., Kondreddi et al, *Journal of Medicinal Chemistry,* 2013, dx.doi.org/10.1021/jm4012774; Lun et al, *Nat. Commun.* 2013, 4:2907; Onajole et al, *Journal of Medicinal Chemistry,* 2013, 56:4093-4103; Rao et al, *Sci. Transl. Med.* 2013, 5:214ra168; and Stec et al, *J. Med. Chem.* 2016, 59(13): 6232-6247). IC are bioisosteric isomers of published urea-based *M. tuberculosis* inhibitors and have similar structure activity relationships (see e.g., Brown et al, *Bioorganic & Medicinal Chemistry,* 2011, 19:5585-5595; North et al, *Bioorganic & Medicinal Chemistry,* 2013, 21:2587-2599; and Scherman et al, *Bioorganic & Medicinal Chemistry,* 2012, 20:3255-3262). The expansion of both the chemical space for the published antitubercular IC compounds and the spectrum of antimycobacterial activity of such compounds is described herein. In addition, lead compounds have demonstrated a safe pharmacological profile and are inhibitors of the mycolic acid biosynthetic pathway in both TB and NTM strains. Specifically, they inhibit the translocation of trehalose-monomycolate (TMM) to the outer membrane, suggestive of *Mycobacteria* membrane protein large 3 (MmpL3) inhibition. A novel series of highly potent indole-based anti-NTM agents is described herein.

Compounds

The present application provides a compound of Formula I:

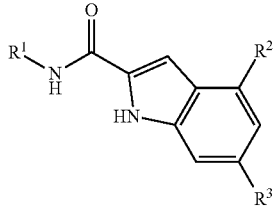

I or a pharmaceutically acceptable salt thereof, wherein:

$R^1$ is selected from the group consisting of $C_{5-10}$ alkyl, $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl, wherein the $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl are each optionally substituted by 1, 2, 3, or 4 substituents independently selected from $C_{1-4}$ alkyl and halo; and $R^2$ and $R^3$ are each independently selected from the group consisting of H and $C_{1-4}$ alkyl.

In some embodiments, $R^1$ is selected from the group consisting of $C_{5-10}$ cycloalkyl, $C_{6-10}$ aryl, —$C_{1-4}$ cycloalkyl, and —$C_{1-4}$ alkyl-$C_{6-10}$ aryl, wherein the $C_{5-10}$ cycloalkyl, $C_{6-10}$ aryl, —$C_{1-4}$ alkyl-$C_{5-11}$) cycloalkyl, and —$C_{1-4}$ alkyl-$C_{6-10}$ aryl are each optionally substituted by 1, 2, 3, or 4 substituents independently selected from $C_{1-4}$ alkyl and halo; and $R^2$ and $R^3$ are each independently selected from the group consisting of H and $C_{1-4}$ alkyl.

In some embodiments, $R^1$ is selected the group consisting of $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl, wherein the $C_{5-10}$ cycloalkyl, $C_{6-10}$ aryl, —$C_{1-4}$ alkyl-$C_{5-10}$ cycloalkyl, and —$C_{1-4}$ alkyl-$C_{6-10}$ aryl are each optionally substituted by 1, 2, 3, or 4 substituents independently selected from $C_{1-4}$ alkyl and halo.

In some embodiments, $R^1$ is selected from the group consisting of $C_{5-10}$ cycloalkyl, —$C_{1-4}$ alkyl-$C_{5-10}$ cycloalkyl, and —$C_{1-4}$ alkyl-$C_{6-10}$ aryl, wherein the $C_{5-10}$ cycloalkyl, —$C_{1-4}$ alkyl-$C_{5-10}$ cycloalkyl, and —$C_{1-4}$ alkyl-$C_{6-10}$ aryl are each optionally substituted by 1, 2, 3, or 4 substituents independently selected from $C_{1-4}$ alkyl and halo.

In some embodiments, $R^1$ is selected from the group consisting of $C_{5-10}$ cycloalkyl, —$C_{1-4}$ alkyl-$C_{5-10}$ cycloalkyl, and —$C_{1-4}$ alkyl-phenyl, wherein the $C_{5-10}$ cycloalkyl, —$C_{1-4}$ alkyl-$C_{5-10}$ cycloalkyl, and —$C_{1-4}$ alkyl-phenyl are each optionally substituted by 1, 2, or 3 substituents independently selected from $C_{1-4}$ alkyl and halo.

In some embodiments, $R^1$ is selected from the group consisting of $C_{5-10}$ cycloalkyl, —$CH_2$—$C_{5-10}$ cycloalkyl, —$CH(CH_3)$—$C_{5-10}$ cycloalkyl, and —$CH_2$-phenyl, wherein the $C_{5-10}$ cycloalkyl, —$CH_2$—$C_{5-10}$ cycloalkyl, and —$CH_2$-phenyl are each optionally substituted by 1, 2, or 3 substituents independently selected from methyl and chloro.

In some embodiments, $R^1$ is selected from the group consisting of monocyclic $C_{5-10}$ cycloalkyl, bicyclic $C_{5-10}$ cycloalkyl, tricyclic $C_{5-10}$ cycloalkyl, —$CH_2$-(tricyclic $C_{5-10}$ cycloalkyl), —$CH(CH_3)$-tricyclic $C_{5-10}$ cycloalkyl, and —$CH_2$-phenyl, wherein the monocyclic $C_{5-10}$ cycloalkyl, bicyclic $C_{5-10}$ cycloalkyl, tricyclic $C_{5-10}$ cycloalkyl, —$CH_2$-(tricyclic $C_{5-10}$ cycloalkyl), —$CH(CH_3)$-tricyclic $C_{5-10}$ cycloalkyl, and —$CH_2$-phenyl, are each optionally substituted by 1, 2, or 3 substituents independently selected from methyl and chloro.

In some embodiments, $R^1$ is selected from the group consisting of monocyclic $C_{5-10}$ cycloalkyl and tricyclic $C_{5-10}$ cycloalkyl. In some embodiments, $R^1$ is selected from adamantyl and cyclooctyl.

In some embodiments, $R^1$ is selected from the group consisting of:

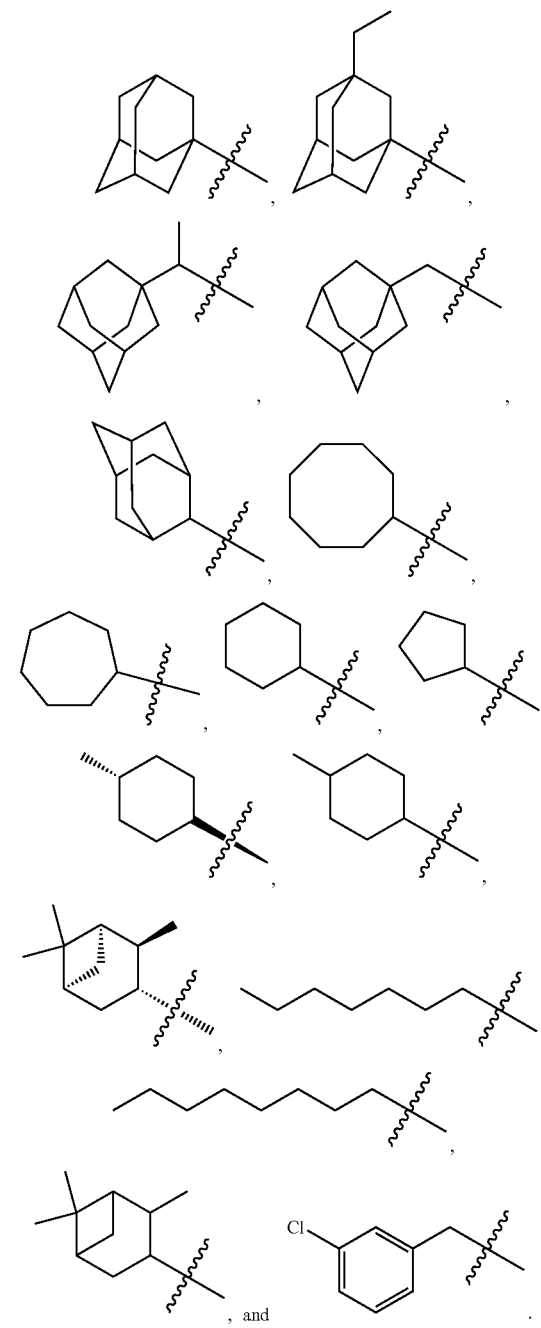

, and

In some embodiments, $R^1$ is selected from the group consisting of:

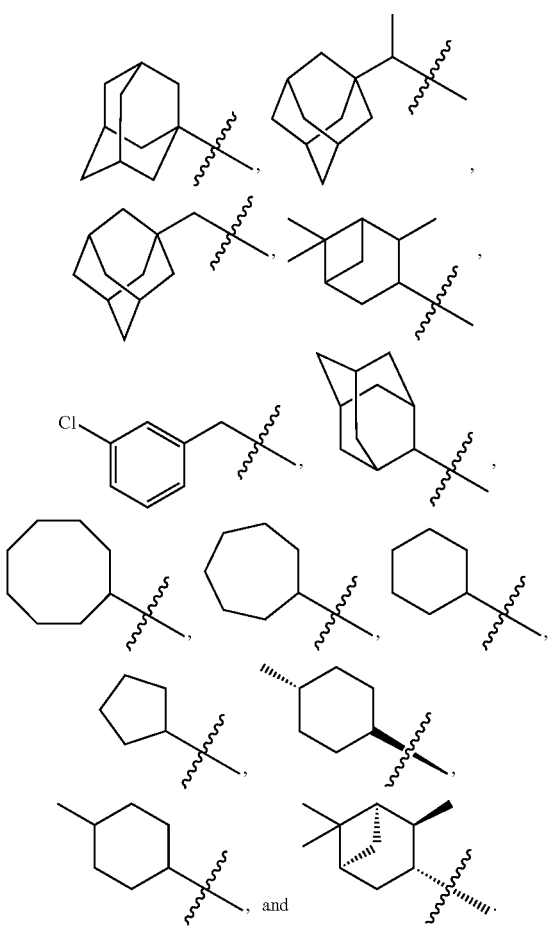

In some embodiments, $R^1$ is selected from the group consisting of:

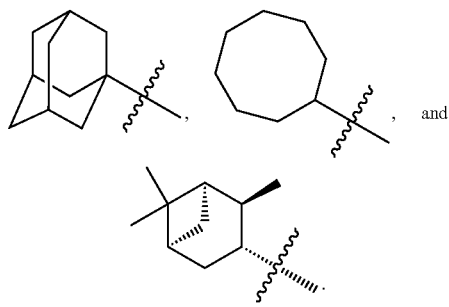

In some embodiments, $R^1$ is selected from the group consisting of:

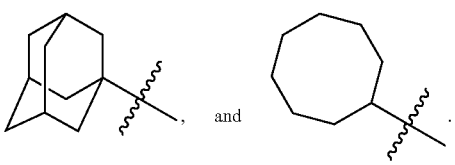 [SMILES: *C12CC3CC(CC(C3)C1)C2 ; *C1CCCCCCC1]

In some embodiments, $R^2$ and $R^3$ are each H.

In some embodiments, $R^2$ and $R^3$ are each $C_{1-4}$ alkyl.

In some embodiments, $R^2$ and $R^3$ are each methyl.

In some embodiments, $R^1$ is selected from the group consisting of $C_{5-10}$ cycloalkyl, —$C_{1-4}$ alkyl-$C_{5-10}$ cycloalkyl, and —$C_{1-4}$ alkyl-$C_{6-10}$ aryl, wherein the $C_{5-10}$ cycloalkyl, —$C_{1-4}$ alkyl-$C_{5-10}$ cycloalkyl, and —$C_{1-4}$ alkyl-$C_{6-10}$ aryl are each optionally substituted by 1, 2, 3, or 4 substituents independently selected from $C_{1-4}$ alkyl and halo; and $R^2$ and $R^3$ are each H or $R^2$ and $R^3$ are each $C_{1-4}$ alkyl.

In some embodiments, $R^1$ is selected from the group consisting of $C_{5-10}$ cycloalkyl, —$CH_2$—$C_{5-10}$ cycloalkyl, —$CH(CH_3)$—$C_{5-10}$ cycloalkyl, and —$CH_2$-phenyl, wherein the $C_{5-10}$ cycloalkyl, —$CH_2$—$C_{5-10}$ cycloalkyl, and —$CH_2$-phenyl are each optionally substituted by 1, 2, or 3 substituents independently selected from methyl and chloro; and $R^2$ and $R^3$ are each H or $R^2$ and $R^3$ are each $C_{1-4}$ alkyl.

In some embodiments, $R^1$ is selected from the group consisting of monocyclic $C_{5-10}$ cycloalkyl, bicyclic $C_{5-10}$ cycloalkyl, tricyclic $C_{5-10}$ cycloalkyl, —$CH_2$-(tricyclic $C_{5-10}$ cycloalkyl), —$CH(CH_3)$-tricyclic $C_{5-10}$ cycloalkyl, and —$CH_2$-phenyl, wherein the monocyclic $C_{5-10}$ cycloalkyl, bicyclic $C_{5-10}$ cycloalkyl, tricyclic $C_{5-10}$ cylcoalkyl, —$CH_2$-(tricyclic $C_{5-10}$ cycloalkyl), —$CH(CH_3)$-tricyclic $C_{5-10}$ cycloalkyl, and —$CH_2$-phenyl, are each optionally substituted by 1, 2, or 3 substituents independently selected from methyl and chloro; and $R^2$ and $R^3$ are each H or $R^2$ and $R^3$ are each methyl.

In some embodiments, the compound of Formula I is selected from the group consisting of:

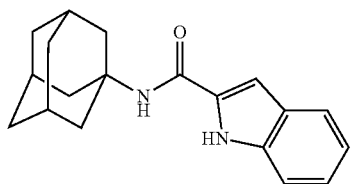

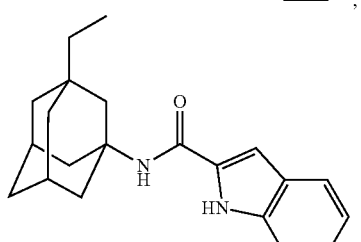

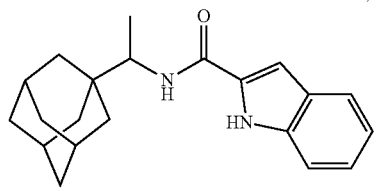

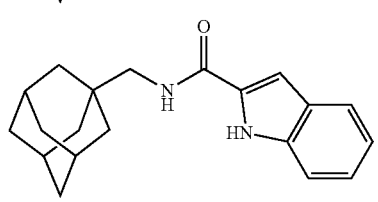

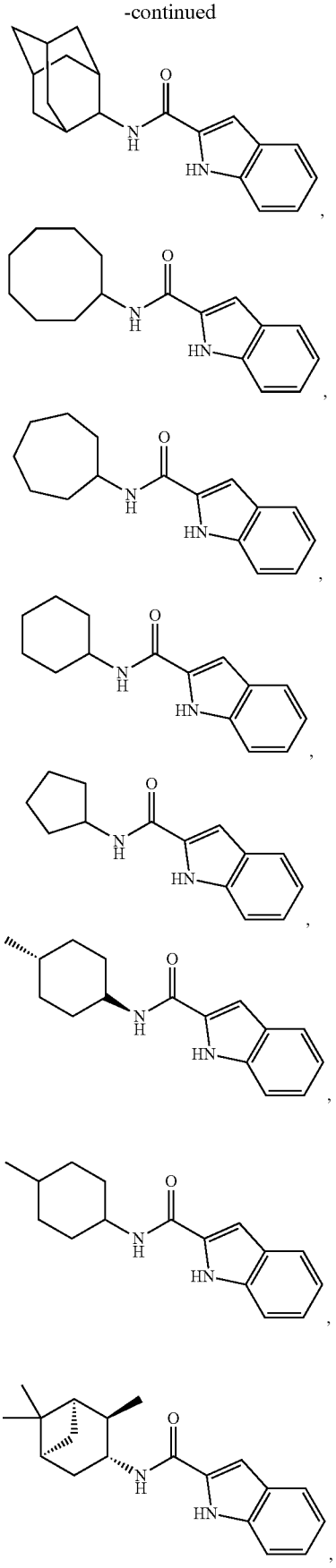
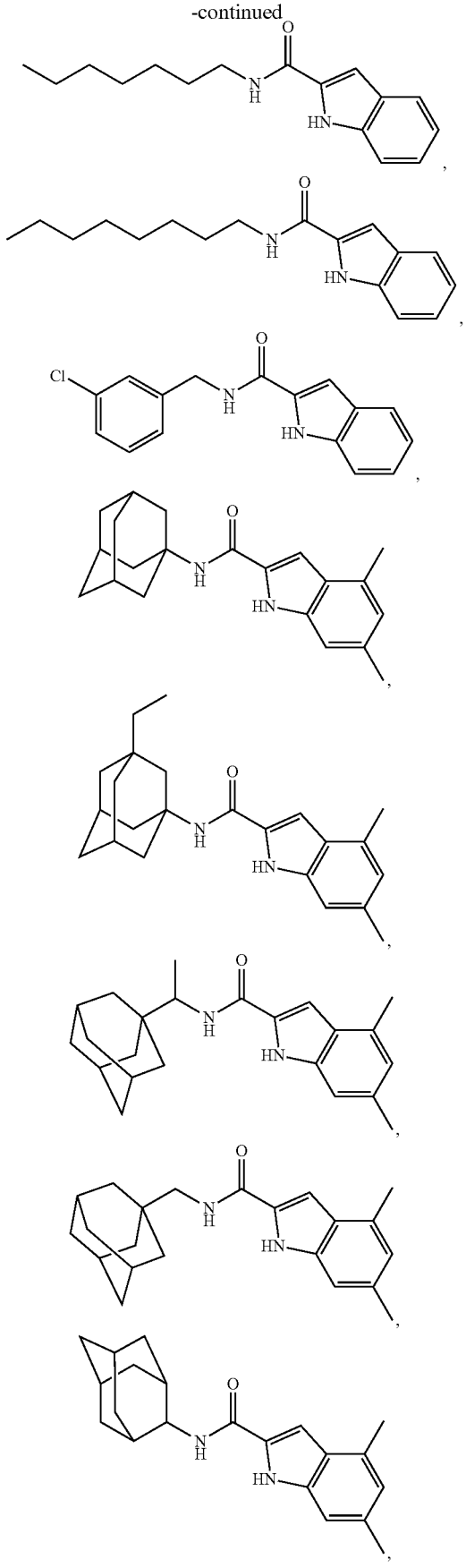

19
-continued
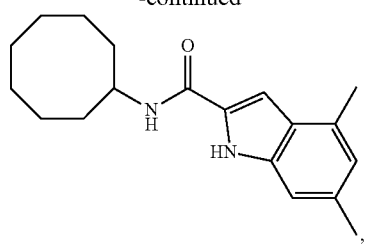
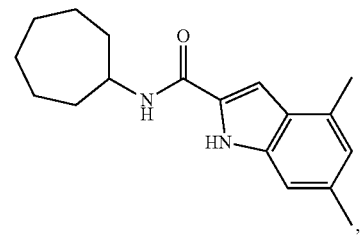
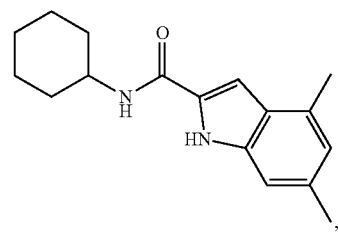
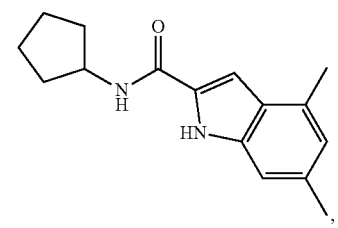
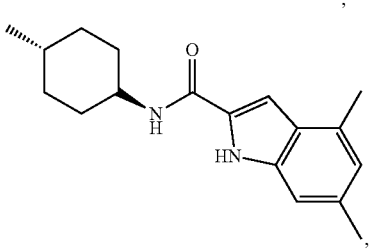
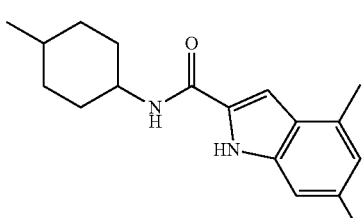
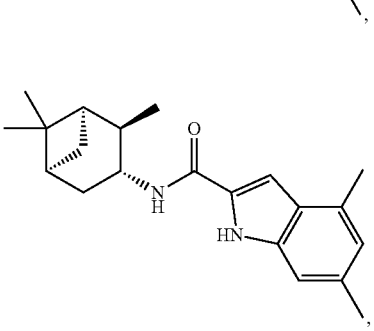
20
-continued
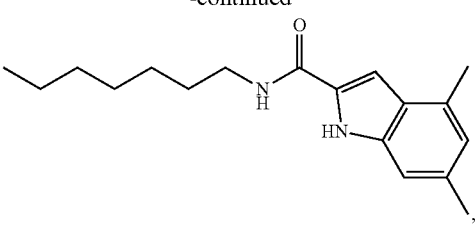
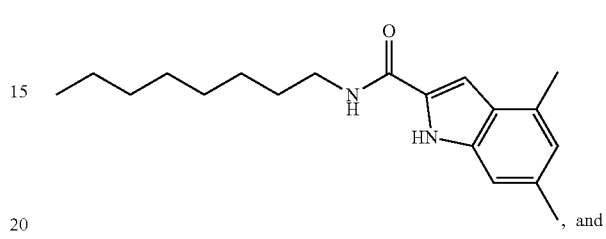
, and
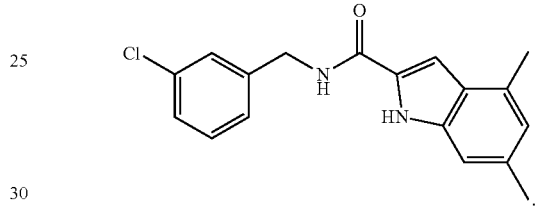
.
In some embodiments, the compound of Formula I is selected from the group consisting of:
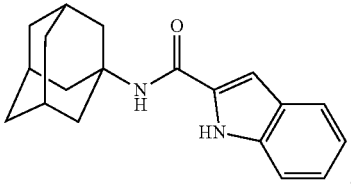
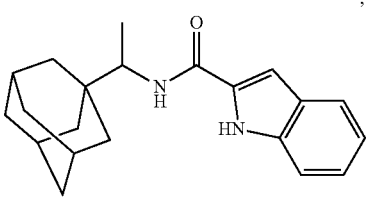
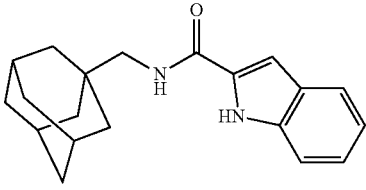

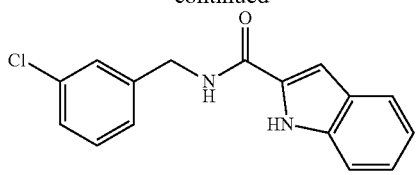
,
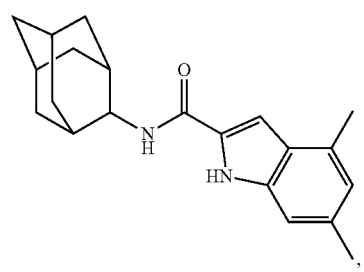
,
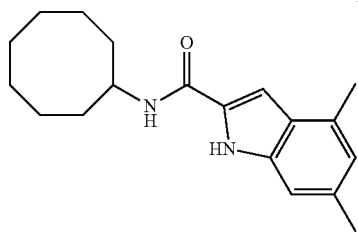
,
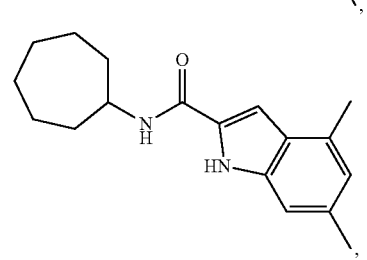
,
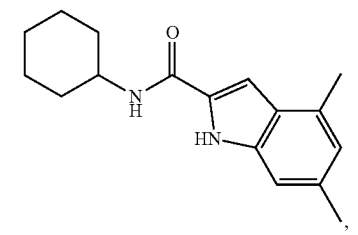
,
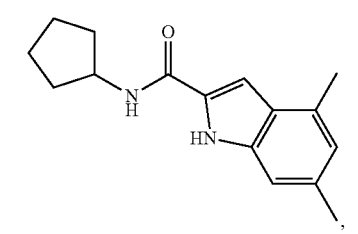
,
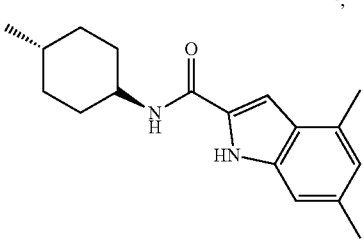
,
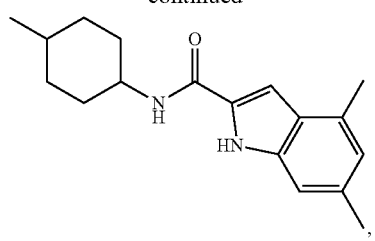
,
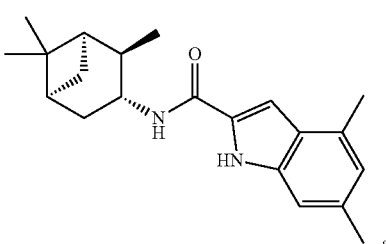
, and
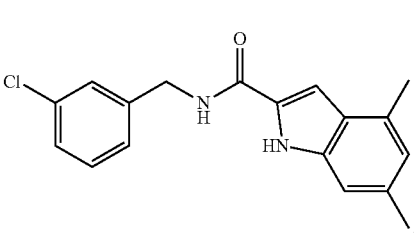
;
or a pharmaceutically acceptable salt thereof.
In some embodiments, the compound of Formula I is selected from the group consisting of:
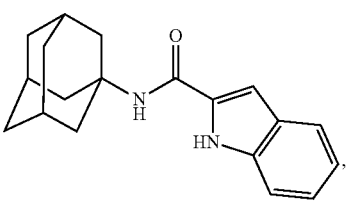
,
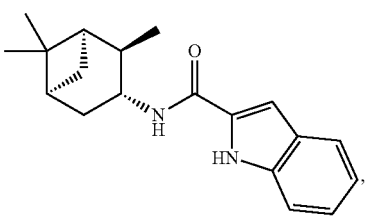
,
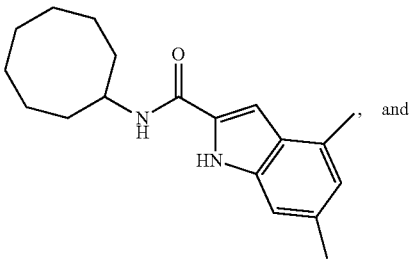
, and

23

-continued

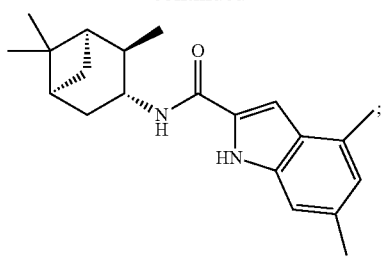

or a pharmaceutically acceptable salt thereof.

In some embodiments, the compound of Formula I is selected from the group consisting of:

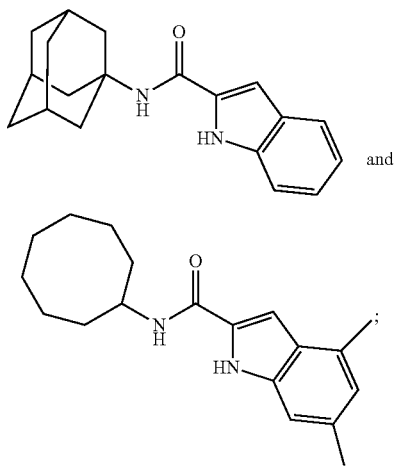

or a pharmaceutically acceptable salt thereof.

Synthesis

Indole-2-carboxamide (IC) compounds of Formula I were generated using published methods and is shown in Scheme 1 (see e.g., Onajole et al, *Journal of Medicinal Chemistry*, 2013, 56:4093-4103). Briefly, the reaction of the arylhydrazine with ethyl pyruvate in the presence of p-toluenesulfonic acid (pTsOH) afforded ethyl indole-2-carboxylate (step a). After NaOH-mediated saponification of the ester (step b), commercially available amines were coupled to indole-2-carboxylic acid using standard coupling conditions (step c).

Scheme 1.

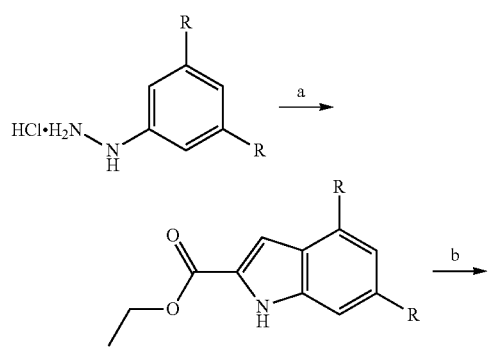

24

-continued

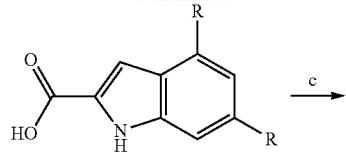

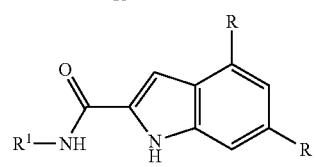

R = H or alkyl

It will be appreciated by one skilled in the art that the processes described are not the exclusive means by which compounds provided herein may be synthesized. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

At various places in the present specification, divalent linking substituents are described. It is specifically intended that each divalent linking substituent include both the forward and backward forms of the linking substituent. For example, —NR(CR'R")$_n$—includes both —NR(CR'R")$_n$— and —(CR'R")$_n$NR—. Where the structure clearly requires a linking group, the Markush variables listed for that group are understood to be linking groups.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl" refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "aryl" refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to about 10 carbon atoms (i.e., a $C_{6-10}$ aryl). In some embodiments, the aryl group is a substituted or unsubstituted phenyl.

As used herein, "halo" refers to fluoro, chloro, bromo, or iodo. In some embodiments, the halo is chloro.

As used herein, "cycloalkyl" refers to non-aromatic cyclic hydrocarbons including cyclized alkyl and/or alkenyl groups. Cycloalkyl groups can include mono- or polycyclic groups (e.g., having 2, 3 or 4 fused rings; bicyclic cycloalkyl groups; and tricyclic cycloalkyl groups) and spirocycles. Cycloalkyl groups can have 5, 6, 7, 8, 9, or 10 ring-forming carbons (i.e., a $C_{5-10}$ cycloalkyl group). In some embodiments, the cycloalkyl is cyclopentyl, cyclohexyl, cycloheptyl, cyclooctyl, cyclononyl, or adamantyl. In some embodiments, the cycloalkyl has 5-10 ring-forming carbon atoms (i.e., a $C_{5-10}$ cycloalkyl group).

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds and salts provided herein are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences,* 17th ed., Mack Publishing Company, Easton, Pa., 1985, p. 1418 and *Journal of Pharmaceutical Science*, 66, 2 (1977). Conventional methods for preparing salt forms are described, for example, in *Handbook of Pharmaceutical Salts: Properties, Selection, and Use*, Wiley-VCH, 2002.

Methods of Use

The present application further provides of a method of treating a non-tuberculosis bacterial infection in a subject in need thereof. As used herein, the term "subject," refers to any animal, including mammals. Example subjects include, but are not limited to, mice, rats, rabbits, dogs, cats, swine, cattle, sheep, horses, primates, and humans. In some embodiments, the subject is a human. In some embodiments, the method comprises administering to the subject a therapeutically effective amount of a compound provided herein (i.e., a compound of Formula I), or a pharmaceutically acceptable salt thereof.

In some embodiments, the non-tuberculosis bacterial infection is caused or involves infection by a non-tuberculosis mycobacterium infection.

In some embodiments, the non-tuberculosis mycobacterium is selected from *M. avium* complex, *M. abscessus* complex, or a combination thereof.

In some embodiments, the non-tuberculosis bacterial mycobacterium is selected from the group consisting of *M. abscessus, M. massiliense, M. bolletii, M. chelonae, M. avium, M. xenopi, M. smegmatis, M. intracellulare, M. chimaera, M. kansasii, M. fortuitum, M. simiae, M. szulgai, M. peregrinum, M. ulcerans, M. marinum, M. haemophilum,* and *M. leprae*. In some embodiments, the non-tuberculosis bacterial mycobacterium is selected from the group consisting of *M. abscessus, M. massiliense, M. bolletii, M. chelonae, M. avium, M. xenopi, M. smegmatis, M. intracellulare, M. chimaera, M. kansasii,* and *M. fortuitum*.

In some embodiments, the non-tuberculosis mycobacterium is selected from the group consisting of *M. xenopi*, the *M. avium* complex (*M. avium, M. intracellulare, M. chimaera*), *M. kansasii, M. fortuitum, M. smegmatis,* and *M. abscessus*. In some embodiments, the non-tuberculosis bacterial mycobacterium is selected from the group consisting of *M. abscessus, M. massiliense, M. bolletii, M. chelonae, M. avium, M. xenopi* and *M. smegmatis*. In some embodiments, the non-tuberculosis mycobacterium is selected from the group consisting of *M. xenopi, M. avium, M. smegmatis,* and *M. abscessus*. In some embodiments, the non-tuberculosis mycobacterium is *M. abscessus*.

In some embodiments, the non-tuberculosis mycobacterium is resistant to one or more antibiotic agents. In some embodiments, the non-tuberculosis mycobacterium is resistant to one or more antibiotic agents selected from the group consisting of isoniazid, rifampicin, ethambutol, and pyrazinamide.

In some embodiments, the non-tuberculosis mycobacterial infection is a hospital acquired mycobacterial infection (e.g., a non-sterile surgical procedure or patient-to-patient transmission, e.g., via fomites). In some embodiments, the non-tuberculosis mycobacterial infection is an environmentally acquired infection (e.g., acquired from contact with contaminated soil, contaminated dust, contaminated water, and the like In some embodiments, the subject is further infected with a Gram-positive or Gram-negative pathogen or a combination thereof. Exemplary Gram-positive pathogens include, but are not limited to, *B. anthracis, E. faecalis, S. Pyogenes, S. pneumoniae, B. subtilis,* and *Staphylococcus aureus*. Exemplary Gram-negative pathogens include, but are not limited to, *Acinetobacter, B. cepacia, E. coli, Klebsiella pneumoniae, P. mirabilis, P. vulgaris, Pseudomonas aeruginosa*. In some embodiments, the subject is further infected with a pathogen which is *Pseudomonas aeruginosa*. In some embodiments, the subject is further infected with a pathogen which is *Staphylococcus aureus*. In some embodiments, the subject is further infected with a combination of *Pseudomonas aeruginosa* and *Staphylococcus aureus*.

In some embodiments, the subject has been identified as having a disease selected from the group consisting of a pulmonary infection, a disease of the central nervous system, a disease of the skin and/or soft tissue, a disseminated infection, or any combination thereof. In some embodiments, the subject has been identified as having a lung disease. In some embodiments, the methods provided herein further comprise identifying the subject as having a lung disease, prior to administering the compound provided herein, or pharmaceutically acceptable salt thereof.

In some embodiments, the methods described herein further comprise treating the pulmonary infection, disease of the central nervous system, disease of the skin and/or soft tissue, disseminated infection, or any combination thereof, in the subject (e.g., treating an infection associated with the pulmonary infection, disease of the central nervous system, disease of the skin and/or soft tissue, disseminated infection, or any combination thereof). In some embodiments, the methods described herein further comprise treating the lung disease in the subject (e.g., treating an infection associated with the lung disease, such as a non-tuberculosis mycobacterial infection). In some embodiments, the lung disease is a structural lung disease. In some embodiments, the lung disease is selected from the group consisting of cystic fibrosis, bronchiectasis, emphysema, and chronic obstructive pulmonary disease, and bronchiectasis. In some embodiments, the lung disease is cystic fibrosis.

In some embodiments, the subject in need thereof is a human subject over the age of 21 years. In some embodiments, the subject is over the age of 30 years, 40 years, 50 years, 60 years, 70 years, 80 years, or 90 years.

In some embodiments, the subject in need thereof is a pediatric subject. As used herein, the term "pediatric subject" refers to a human subject under the age of 21 years. In some embodiments, the pediatric subject is under the age of 18 years, 16 years, 14 years, 12 years, 10 years, 8 years, 6 years, 4 years, 2 years, 12 months, or 6 months. In some embodiments, the lung disease is pediatric cystic fibrosis.

The present application further provides a method of inhibiting mycolic acid transport in a cell or tissue, comprising contacting the cell or tissue with a compound provided herein, or a pharmaceutically acceptable salt thereof. In some embodiments, the contacting can be performed in vitro. In some embodiments, the contacting can be performed in vivo.

The present application further provides a method of inhibiting translocation of trehalose-monomycolate in a cell or tissue, comprising contacting the cell or tissue with a compound provided herein, or a pharmaceutically acceptable salt thereof. In some embodiments, the contacting can be performed in vitro. In some embodiments, the contacting can be performed in vivo.

The present application further provides a method of inhibiting mycobacterium membrane protein large 3 (MmpL3) in a cell or tissue, comprising contacting the cell or tissue with a compound provided herein, or a pharmaceutically acceptable salt thereof. In some embodiments, the contacting can be performed in vitro. In some embodiments, the contacting can be performed in vivo.

The present application further provides a method of inhibiting mycolic acid transport in a subject, comprising administering to the subject a compound provided herein, or a pharmaceutically acceptable salt thereof. In some embodiments, the method comprises inhibiting mycolic acid transport in a subject infected with a non-tuberculosis mycobacterium. In some embodiments, the non-tuberculosis mycobacterium is selected from *M. avium* complex, *M. abscessus* complex, or a combination thereof. In some embodiments, the non-tuberculosis bacterial mycobacterium is selected from the group consisting of *M. abscessus, M. massiliense, M. bolletii, M. chelonae, M. avium, M. xenopi, M. smegmatis, M. intracellulare, M. chimaera, M. kansasii, M. fortuitum, M. simiae, M. szulgai, M. peregrinum, M. ulcerans, M. marinum, M. haemophilum*, and *M. leprae*. In some embodiments, the non-tuberculosis bacterial mycobacterium is selected from the group consisting of *M. abscessus, M. massiliense, M. bolletii, M. chelonae, M. avium, M. xenopi, M. smegmatis, M. intracellulare, M. chimaera, M. kansasii*, and *M. fortuitum*. In some embodiments, the non-tuberculosis mycobacterium is selected from the group consisting of *M. xenopi*, the *M. avium* complex (*M. avium, M. intracellulare, M. chimaera*), *M. kansasii, M. fortuitum, M. smegmatis*, and *M. abscessus*. In some embodiments, the non-tuberculosis bacterial mycobacterium is selected from the group consisting of *M. abscessus, M. massiliense, M. bolletii, M. chelonae, M. avium, M. xenopi* and *M. smegmatis*. In some embodiments, the non-tuberculosis mycobacterium is selected from the group consisting of *M. xenopi, M. avium, M. smegmatis*, and *M. abscessus*. In some embodiments, the non-tuberculosis mycobacterium is *M. abscessus*.

The present application further provides a method of inhibiting translocation of trehalose-monomycolate in a subject, comprising administering to the subject a compound provided herein, or a pharmaceutically acceptable salt thereof. In some embodiments, the method comprises inhibiting translocation of trehalose-monomycolate in a subject infected with a non-tuberculosis mycobacterium. In some embodiments, the non-tuberculosis mycobacterium is selected from *M. avium* complex, *M. abscessus* complex, or a combination thereof. In some embodiments, the non-tuberculosis bacterial mycobacterium is selected from the group consisting of *M. abscessus, M. massiliense, M. bolletii, M. chelonae, M. avium, M. xenopi, M. smegmatis, M. intracellulare, M. chimaera, M. kansasii, M. fortuitum, M. simiae, M. szulgai, M. peregrinum, M. ulcerans, M. marinum, M. haemophilum*, and *M. leprae*. In some embodiments, the non-tuberculosis bacterial mycobacterium is selected from the group consisting of *M. abscessus, M. massiliense, M. bolletii, M. chelonae, M. avium, M. xenopi, M. smegmatis, M. intracellulare, M. chimaera, M. kansasii*, and *M. fortuitum*. In some embodiments, the non-tuberculosis mycobacterium is selected from the group consisting of *M. xenopi*, the *M. avium* complex (*M. avium, M. intracellulare, M. chimaera*), *M. kansasii, M. fortuitum, M. smegmatis*, and *M. abscessus*. In some embodiments, the non-tuberculosis bacterial mycobacterium is selected from the group consisting of *M. abscessus, M. massiliense, M. bolletii, M. chelonae, M. avium, M. xenopi* and *M. smegmatis*. In some embodiments, the non-tuberculosis mycobacterium is selected from the group consisting of *M. xenopi, M. avium, M. smegmatis*, and *M. abscessus*. In some embodiments, the non-tuberculosis mycobacterium is *M. abscessus*.

The present application further provides a method of inhibiting mycobacterium membrane protein large 3 (MmpL3) in a subject, comprising administering to the subject a compound provided herein, or a pharmaceutically acceptable salt thereof. In some embodiments, the method comprises inhibiting mycobacterium membrane protein large 3 (MmpL3) in a subject infected with a non-tuberculosis mycobacterium. In some embodiments, the non-tuberculosis mycobacterium is selected from *M. avium* complex, *M. abscessus* complex, or a combination thereof. In some embodiments, the non-tuberculosis bacterial mycobacterium is selected from the group consisting of *M. abscessus, M. massiliense, M. bolletii, M. chelonae, M. avium, M. xenopi, M. smegmatis, M. intracellulare, M. chimaera, M. kansasii, M. fortuitum, M. simiae, M. szulgai, M. peregrinum, M. ulcerans, M. marinum, M. haemophilum*, and *M. leprae*. In some embodiments, the non-tuberculosis bacterial mycobacterium is selected from the group consisting of *M. abscessus, M. massiliense, M. bolletii, M. chelonae, M. avium, M. xenopi, M. smegmatis, M. intracellulare, M. chimaera, M. kansasii*, and *M. fortuitum*. In some embodiments, the non-tuberculosis mycobacterium is selected from the group consisting of *M. xenopi*, the *M. avium* complex (*M. avium, M. intracellulare, M. chimaera*), *M. kansasii, M. fortuitum, M. smegmatis*, and *M. abscessus*. In some embodiments, the non-tuberculosis bacterial mycobacterium is selected from the group consisting of *M. abscessus, M. massiliense, M. bolletii, M. chelonae, M. avium, M. xenopi* and *M. smegmatis*. In some embodiments, the non-tuberculosis mycobacterium is selected from the group consisting of *M. xenopi, M. avium, M. smegmatis*, and *M. abscessus*. In some embodiments, the non-tuberculosis mycobacterium is *M. abscessus*.

The present application further provides a method of treating a non-tuberculosis mycobacterial infection in a subject in need thereof, comprising:
i) detecting an infection in the subject that is caused or involves infection by a non-tuberculosis mycobacterium; and
ii) administering to the subject a therapeutically effective amount of a compound provided herein, or a pharmaceutically acceptable salt thereof.

In some embodiments, prior to the detecting of step i), the subject has been identified as having a disease selected from the group consisting of a lung disease, a pulmonary infection, a disease of the central nervous system, a disease of the skin and/or soft tissue, a disseminated infection, or any combination thereof. In some embodiments, prior to the detecting of step i), the subject has been identified as having a lung disease. In some embodiments, the subject has been identified as having a structural lung disease. In some embodiments, the subject has been identified as having a lung disease selected from the group consisting of cystic fibrosis, bronchiectasis, emphysema, chronic obstructive pulmonary disease, and bronchiectasis. In some embodiments, the subject has been identified as having a lung disease which is cystic fibrosis.

In some embodiments, the subject in need thereof is a human subject over the age of 21 years. In some embodiments, the subject is over the age of 30 years, 40 years, 50 years, 60 years, 70 years, 80 years, or 90 years. In some embodiments, the subject is a pediatric subject. In some embodiments, the pediatric subject has been identified as having a lung disease which is pediatric cystic fibrosis.

In some embodiments, the non-tuberculosis mycobacterium is selected from *M. avium* complex, *M. abscessus* complex, or a combination thereof. In some embodiments, the non-tuberculosis bacterial mycobacterium is selected from the group consisting of *M. abscessus, M. massiliense, M. bolletii, M. chelonae, M. avium, M. xenopi, M. smegmatis, M. intracellulare, M. chimaera, M. kansasii, M. fortuitum, M. simiae, M. szulgai, M. peregrinum, M. ulcerans, M.

*marinum, M. haemophilum*, and *M. leprae*. In some embodiments, the non-tuberculosis bacterial mycobacterium is selected from the group consisting of *M. abscessus, M. massiliense, M. bolletii, M. chelonae, M. avium, M. xenopi, M. smegmatis, M. intracellulare, M. chimaera, M. kansasii,* and *M. fortuitum*. In some embodiments, the non-tuberculosis mycobacterium is selected from the group consisting of *M. xenopi,* the *M. avium* complex (*M. avium, M. intracellulare, M. chimaera*), *M. kansasii, M. fortuitum, M. smegmatis,* and *M. abscessus*. In some embodiments, the non-tuberculosis bacterial mycobacterium is selected from the group consisting of *M. abscessus, M. massiliense, M. bolletii, M. chelonae, M. avium, M. xenopi* and *M. smegmatis*. In some embodiments, the non-tuberculosis mycobacterium is selected from the group consisting of *M. xenopi, M. avium, M. smegmatis,* and *M. abscessus*. In some embodiments, the non-tuberculosis mycobacterium is *M. abscessus*.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the infection or disease; for example, inhibiting an infection, disease, condition, or disorder in an individual who is experiencing or displaying the pathology or symptomatology of the infection, disease, condition, or disorder (i.e., arresting further development of the pathology and/or symptomatology); and (2) ameliorating the infection or disease; for example, ameliorating an infection, disease, condition, or disorder in an individual who is experiencing or displaying the pathology or symptomatology of the infection, disease, condition, or disorder (i.e., reversing the pathology and/or symptomatology) such as decreasing the severity of the infection or disease or reducing or alleviating one or more symptoms of the infection or disease.

Combination Therapies

One or more additional therapeutic agents such as, for example, antibacterial agents, anti-inflammatory agents, steroids, and anesthetics (e.g., for use in combination with a surgical procedure) can be used in combination with the compounds and salts provided herein for treatment of a non-tuberculosis bacterial infection (e.g., the non-tuberculosis mycobacterial infection) or disease identified in the subject (e.g., lung disease, pulmonary infection, disease of the central nervous system, disease of the skin and/or soft tissue, disseminated infection, or any combination thereof), described herein.

Example antibacterial agents include, but are not limited to, aminoglycosides (e.g., gentamicin, neomycin, streptomycin, ciprofloxacin, and tobramycin), penicillins (e.g., amoxicillin, ampicillin, meropenem), macrolides (e.g., erythromycin), rifampicin, bedaquiline, and clofazimine.

Example anti-inflammatory agents include, but are not limited to, aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxicam, rofecoxib, salsalate, sodium salicylate, sulindac, tolmetin sodium, and valdecoxib.

Example steroids include, but are not limited to, corticosteroids such as cortisone, dexamethasone, hydrocortisone, methylprednisolone, prednisolone, and prednisone.

Example anesthetics include, but are not limited to, local anesthetics (e.g., lidocaine, procain, ropivacaine) and general anesthetics (e.g., desflurane, enflurane, halothane, isoflurane, methoxyflurane, nitrous oxide, sevoflurane, mmobarbital, methohexital, thiamylal, thiopental, diazepam, lorazepam, midazolam, etomidate, ketamine, propofol, alfentanil, fentanyl, remifentanil, buprenorphine, butorphanol, hydromorphone levorphanol, meperidine, methadone, morphine, nalbuphine, oxymorphone, pentazocine).

In some embodiments, the additional therapeutic agent is administered simultaneously with a compound or salt provided herein. In some embodiments, the additional therapeutic agent is administered after administration of the compound or salt provided herein. In some embodiments, the additional therapeutic agent is administered prior to administration of the compound or salt provided herein. In some embodiments, the compound or salt provided herein is administered during a surgical procedure. In some embodiments, the compound or salt provided herein is administered in combination with an additional therapeutic agent during a surgical procedure.

Pharmaceutical Compositions

When employed as pharmaceuticals, the compounds and salts provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (e.g., transdermal, epidermal, ophthalmic and to mucous membranes including intranasal, vaginal, and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided are pharmaceutical compositions which contain, as the active ingredient, a compound provided herein, or a pharmaceutically acceptable salt thereof, in combination with one or more pharmaceutically acceptable carriers (e.g., excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

The active ingredient can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

EXAMPLES

Figure 1B:
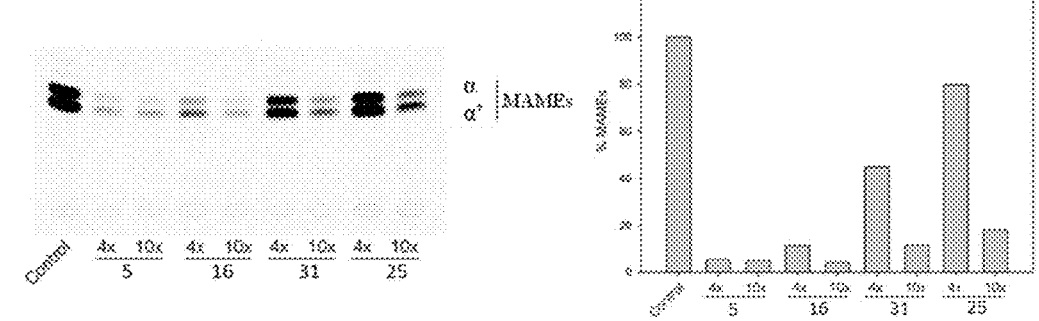

The compounds described herein have been synthesized and tested against a panel of mycobacteria including *M. abscessus, M. massiliense, M. bollettii, M. chelonae, M. avium, M. xenopi, M. tuberculosis*, and *M. smegmatis*. Eight compounds exhibited highly potent anti-NTM activity with sub-μg/mL minimum inhibitor concentrations (MIC) in the range of 0.0039-0.25 μg/mL. Interestingly, seven compounds showed highly potent activity against *M. xenopi*, with sub-μg/mL MIC values in the range of 0.06-1 μg/mL. Four compounds had activity against *M. avium*, with MIC values in the range of 0.25-8 μg/mL. Drug-resistant *M. smegmatis* strains were generated to the active compounds which show mutations in the mmpl3 gene, which is the gene that codes for the mycolic acid transporter, MmpL3. MmpL proteins are conserved across all mycobacterial species and are presumed to be the target for these indole-based compounds. Macromolecular analysis of *M. abscessus* treated with the indole-based compounds show the inhibition of mycolic acid transport, further indicating that these compounds are inhibiting NTM MmpL proteins, as shown in FIGS. 1A-1B. Minimum bactericidal concentrations (MBC) have been determined for four IC compounds (5, 16, 25, and 31) that show potent MBC values similar to corresponding MIC values.

All chemicals and solvents were purchased from commercial sources. The chemical reactions were tracked by TLC using Biotage Silica Gel 60F254 plates and spots were visualized by UV lamp or $I_2$ condensation. Compounds were purified using a Biotage SP silica gel column on a Biotage Isolera One. $^1$H and $^{13}$C NMR were recorded on a 400 MHz Bruker NMR and chemical shifts were reported relative to solvent peak. Analytical RP-HPLC was determined on a Waters Acquity UPLC system equipped with an Acquity BEH C18 column (1.7 μm), flow rate of 0.5 mL/min and a gradient of solvent A (water with 0.1% formic acid) and solvent B (acetonitrile with 0.1% formic acid): 0-0.25 min 97% A; 0.25-3.0 min 3-100% B (linear gradient); 3.0-4.5 min 100% B; 4.5-4.75 min 0-97% A (linear gradient); 4.75-5.0 min 97% A. UV absorbance at 254 nm was used as the detection method. All compounds were found to have >95% purity with the described analytical methods.

Intermediate 1. Ethyl 4,6-dimethyl-1H-indole-2-carboxylate

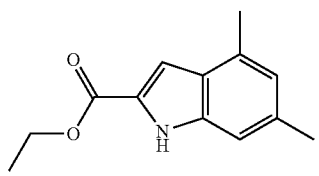 [SMILES: CCOC(=O)c1cc2c(C)cc(C)cc2[nH]1]

p-Toluene sulfonic acid (PTSA, 11.023 g, 55 mmol) was added to 100 mL of benzene and refluxed under Dean-Stark conditions for 2 hours. Ethyl pyruvate (5.04 g, 43 mmol) and 4,6-dimethylphenylhydrazine hydrogen chloride (5.00 g, 23 mmol) were slowly added to the mixture with an additional 0.141 g PTSA and the reaction was refluxed overnight. After cooling to room temperature, the organic layer was neutralized with NaHCO$_3$, extracted twice with EtAc and washed sequentially with 5 M NaHCO$_3$, H$_2$O and brine. Crude product was purified using flash column chromatography with a 0-30% EtAc in hexanes gradient 1.75 mg (27.7%) of tan powder; $^1$H NMR (DMSO-d$_6$) δ=1.32 (3H, t, J=8 Hz), 2.34 (3H, s), 2.43 (3H, s), 4.30 (2H, q, J=8 Hz), 6.69 (1H, s), 7.03 (1H, s), 7.10 (1H, s), 11.67 (1H, s); $^{13}$C NMR (DMSO-d$_6$) δ=14.31, 18.24, 21.52, 60.17, 106.41, 109.53, 122.17, 124.96, 126.04, 130.73, 134.21, 137.69, 161.35; ESI-MS: [M+H]$^+$ calculated for C$_{13}$H$_{16}$NO$_2$: 218.1, found: 218.1.

Intermediate 2.
4,6-Dimethyl-1H-indole-2-carboxylic acid

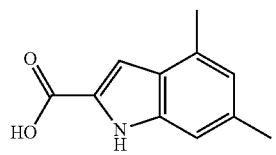

A mixture of ethyl 4,6-dimethyl-1H-indole-2-carboxylate (Intermediate 1, 500 mg, 2.6 mmol), EtOH (5 mL) and NaOH (460 mg, 11.5 mmol) was heated under reflux for 6 hours. The solvent was removed by evaporation, and the solid was dissolved in 50 mL H$_2$O and acidified with 6 N HCl to pH 3. The white precipitate formed upon acidification was recovered via filtration. 438 mg (>99%) of white powder; $^1$H NMR (DMSO-d$_6$) δ=2.34 (3H, s), 2.42 (3H, s), 6.68 (1H, s), 7.02 (1H, s), 7.04 (1H, s), 11.54, (1H, s), 12.74, (1H, s); $^{13}$C NMR (DMSO-d$_6$) δ=18.26, 21.51, 106.03, 109.49, 121.96, 125.07, 127.10, 130.56, 133.79, 137.53, 162.83: [M+H]$^+$ calculated for C$_{11}$H$_{10}$NO$_2$: 188.1, found: 187.8.

Example 1

General Synthetic Method for Unsubstituted Indole-2-caboxamides

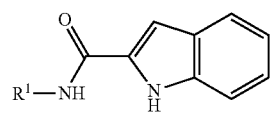

Indole-2-carboxamide (1.5 eq), DCC (1.2 eq), DMAP (0.1 eq) and an appropriately substituted amine (1.0 eq) were all dissolved in anhydrous CH$_2$Cl$_2$ (10 mL/1.0 mmol amine) and stirred at room temperature for 24 hours. The evolved precipitate was filtered and the filtrate was removed under reduced pressure. The residue was purified by normal phase flash column chromatography using a hexane to ethyl acetate gradient.

Examples 2-16 were prepared according to the general procedures described in Example 1 using appropriately substituted starting materials.

Example 2

N-(1-adamantyl)-1H-indole-2-carboxamide
(Compound 5)

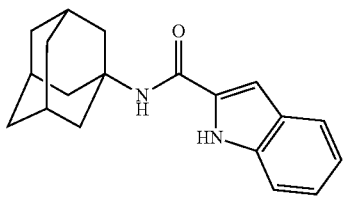 [SMILES: O=C(NC12CC3CC(CC(C3)C1)C2)c1cc2ccccc2[nH]1]

197 mg (33.5%) of white powder; $^1$H NMR (CDCl$_3$) δ=1.75 (6H, br), 2.18 (9H, br), 5.92 (1H, s), 6.76 (1H, s), 7.12 (1H, t, J=8 Hz), 7.25 (1H, t, J=8 Hz), 7.50 (1H, d, J=8 Hz), 7.61 (1H, s, 8 Hz) 9.99 (1H, s); $^{13}$C NMR (CDCl$_3$) δ=29.52, 36.36, 41.86, 52.50, 101.18, 112.14, 120.42, 121.69, 124.04, 127.68, 131.93, 136.41, 160.93; ESI-MS: [M+H]$^+$ calculated for C$_{19}$H$_{23}$N$_2$O: 295.2, found: 295.0.

Example 3

N-(3-ethyl-1-adamantyl)-1H-indole-2-carboxamide
(Compound 6)

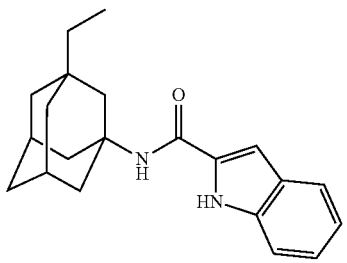 [SMILES: CCC12CC3CC(C1)CC(NC(=O)c1cc4ccccc4[nH]1)(C3)C2]

189 mg (29.3%) of white powder; $^1$H NMR (CDCl$_3$) δ=0.83 (3H, t, J=8 Hz), 1.21 (2H, q, J=8 Hz), 1.44-1.52 (4H, m), 1.60-1.73 (2H, m), 1.88 (2H, s), 2.07-2.15 (4H, m), 2.21 (2H, s), 5.92 (1H, s), 6.75 (1H, s), 7.12 (1H, t, J=8 Hz), 7.26 (1H, t, J=8 Hz), 7.50 (1H, d, J=8 Hz), 7.61 (1H, d, J=8 Hz), 9.94 (1H, s); $^{13}$C NMR (CDCl$_3$) δ=7.05, 29.70, 34.61, 35.85, 35.95, 40.76, 41.46, 46.08, 53.37, 101.14, 112.06, 120.45, 121.70, 124.08, 127.68, 131.86, 136.27, 160.86; ESI-MS: [M+H]$^+$ calculated for C$_{21}$H$_{27}$N$_2$O: 323.2, found: 323.2.

Example 4

N-(1-(1-adamantyl)ethyl)-1H-indole-2-carboxamide
(Compound 7)

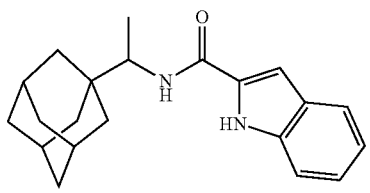 [SMILES: CC(NC(=O)c1cc2ccccc2[nH]1)C12CC3CC(CC(C3)C1)C2]

198 mg (30.7%) of white powder; $^1$H NMR (CDCl$_3$) δ=1.17 (3H, d, J=4 Hz), 1.58-1.74 (12H, m), 2.01 (3H, s), 4.03 (1H, t, J=8 Hz), 6.13 (1H, d, J=8 Hz), 6.86 (1H, s), 7.12 (1H, t, J=8 Hz), 7.26 (1H, t, J=8 Hz), 7.45 (1H, d, J=8 Hz), 7.62 (1H, d, J=8 Hz), 10.26 (1H, s); $^{13}$C NMR (CDCl$_3$) δ=14.66, 28.29, 36.19, 37.01, 38.49, 53.18, 101.15, 111.95, 120.63, 121.74, 124.34, 127.63, 131.10, 136.18, 161.03; ESI-MS: [M+H]$^+$ calculated for C$_{21}$H$_{27}$N$_2$O: 323.4, found: 323.3.

Example 5

N-(1-(1-adamantyl)methyl)-1H-indole-2-carboxamide (Compound 8)

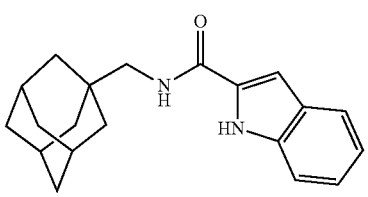 [SMILES: O=C(NCC12CC3CC(CC(C3)C1)C2)c1cc2ccccc2[nH]1]

266 mg (43.1%) of white powder; $^1$H NMR (CDCl$_3$) δ=1.17 (3H, d, J=4 Hz), 1.58-1.74 (13H, m), 4.03 (1H, quin, J=8 Hz), 6.13 (1H, d, J=4 Hz), 6.86 (1H, s), 7.12 (1H, t, J=8 Hz), 7.26 (1H, t, J=8 Hz), 7.45 (1H, d, J=8 Hz), 7.62 (1H, d, J=8 Hz), 10.26 (1H, s); $^{13}$C NMR (CDCl$_3$) δ=28.19, 34.13, 36.88, 40.27, 50.98, 101.32, 111.90, 120.67, 121.80, 124.42, 129.51, 130.90, 136.12, 161.68; ESI-MS: [M+H]$^+$ calculated for C$_{20}$H$_{25}$N$_2$O: 309.4, found: 309.3

Example 6

N-(2-adamantyl)-1H-indole-2-carboxamide
(Compound 9)

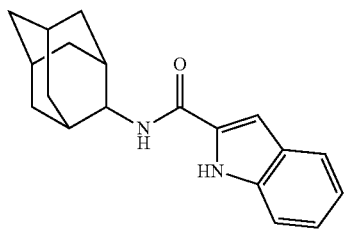 [SMILES: O=C(NC1C2CC3CC(C2)CC1C3)c1cc2ccccc2[nH]1]

202 mg (34.3%) of white powder; $^1$H NMR (CDCl$_3$) δ=1.72 (1H, s), 1.75 (1H, s), 1.80 (1H, s), 1.88 (1H, s), 1.92 (8H, s), 2.09 (2H, s), 4.29 (1H, d, J=8 Hz), 6.50 (1H, d, J=8 Hz), 6.86 (1H, s), 7.14 (1H, t, J=8 Hz), 7.28 (1H, t, J=8 Hz), 7.44 (1H, d, J=8 Hz), 7.64 (1H, d, J=8 Hz), 9.54 (1H, s); $^{13}$C NMR (CDCl$_3$) δ=27.23, 32.04, 37.13, 27.50, 53.54, 101.33, 111.99, 120.62, 121.78, 124.34, 127.69, 131.23, 136.26, 160.76; ESI-MS: [M+H]$^+$ calculated for C$_{19}$H$_{23}$N$_2$O: 295.4, found: 295.3.

Example 7

N-cyclooctyl-1H-indole-2-carboxamide (Compound 10)

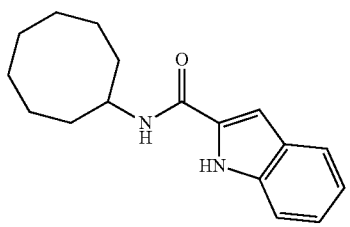 [SMILES: O=C(NC1CCCCCCC1)c1cc2ccccc2[nH]1]

233 mg (43.1%) of white powder; ¹H NMR (CDCl₃) δ=1.62-1.72 (13H, m), 1.96-2.01 (2H, m), 4.25 (1H, sep, J=4 Hz), 6.10 (1H, d, J=8 Hz), 6.80 (1H, s), 7.14 (1H, t, J=4 Hz), 7.28 (1H, t, J=4 Hz), 7.44 (1H, d, J=8 Hz), 7.63 (1H, d, J=8 Hz), 9.49 (1H, s); ¹³C NMR (CDCl₃) δ=23.73, 27.19, 32.46, 49.71, 101.33, 111.96, 120.59, 121.80, 124.31, 127.69, 131.18, 136.21, 160.4; ESI-MS: [M+H]⁺ calculated for $C_{17}H_{24}N_2O$: 271.4, found: 271.4.

Example 8

N-cycloheptyl-1H-indole-2-carboxamide (Compound 11)

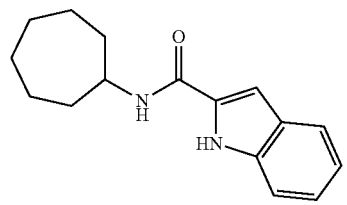 [SMILES: O=C(NC1CCCCCC1)c1cc2ccccc2[nH]1]

231 mg (45.1%) of white powder; ¹H NMR (CDCl₃) δ=1.57-1.69 (8H, m), 1.71-1.94 (2H, m), 2.04-2.08 (2H, m), 4.19 (1H, quin, J=4 Hz), 6.09 (1H, d, J=8 Hz), 6.80 (1H, s), 7.14 (1H, t, J=4 Hz), 7.28 (1H, t, J=8 Hz), 7.43 (1H, d, J=8 Hz), 7.63 (1H, d, J=8 Hz), 9.41 (1H, s); ¹³C NMR (CDCl₃) δ=24.14, 23.04, 31.05, 50.78, 101.36, 111.71, 111.94, 120.61, 121.82, 124.34, 127.69, 131.15, 136.19, 160.46; ESI-MS: [M+H]⁺ calculated for $C_{16}H_{21}N_2O$: 257.3, found: 257.2.

Example 9

N-cyclohexyl-1H-indole-2-carboxamide (Compound 12)

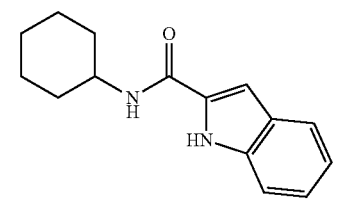 [SMILES: O=C(NC1CCCCC1)c1cc2ccccc2[nH]1]

233 mg (48.1%) of white powder; ¹H NMR (CDCl₃) δ=1.11 (1H, quin, J=8 Hz), 1.18-1.47 (5H, m), 1.66 (1H, s), 1.76-1.95 (4H, m), 2.05 (1H, d, J=8 Hz), 6.00 (1H, d, J=8 Hz), 7.14 (1H, t, J=8 Hz), 7.28 (1H, t, J=8 Hz), 7.43 (1H, d, J=8 Hz), 7.63 (1H, d, J=8 Hz), 9.29 (1H, s); ¹³C NMR (CDCl₃) δ=24.60, 24.92, 25.54, 32.44, 33.32, 48.54, 101.39, 106.48, 111.89, 120.63, 121.85, 124.38, 127.71, 136.13, 160.64; ESI-MS: [M+H]⁺ calculated for $C_{15}H_{19}N_2O$: 243.3, found: 243.3.

Example 10

N-cyclopentyl-1H-indole-2-carboxamide (Compound 13)

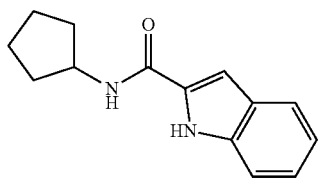 [SMILES: O=C(NC1CCCC1)c1cc2ccccc2[nH]1]

277 mg (60.7%) of white powder; ¹H NMR (CDCl₃) δ=1.54 (2H, quin, J=4 Hz), 1.66-1.77 (4H, m), 2.11 (2H, sex, J=4 Hz), 4.43 (1H, sex, J=4 Hz), 6.09 (1H, d, J=4 Hz), 6.80 (1H, s), 7.13 (1H, t, J=8 Hz), 7.28 (1H, t, J=8 Hz), 7.43 (1H, d, J=8 Hz), 7.63 (1H, d, J=8 Hz), 9.41 (1H, s); ¹³C NMR (CDCl₃) δ=23.81, 26.16, 33.32, 51.49, 101.47, 111.94, 120.62, 121.85, 124.38, 127.70, 131.01, 136.19, 161.22; ESI-MS: [M+H]⁺ calculated for $C_{14}H_{17}N_2O$: 229.3, found: 229.2.

Example 11

N-((1s,4s)-4-methylcyclohexyl)-1H-indole-2-carboxamide (Compound 14)

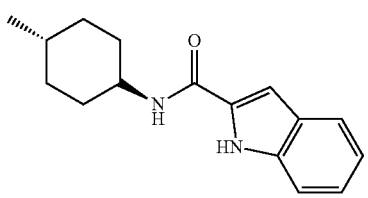

277 mg (54.0%) of white powder; ¹H NMR (CDCl₃) δ=1.04-1.15 (4H, m), 1.33 (3H, q, J=8 Hz), 1.56-1.67 (3H, m), 1.87 (5H, d, J=4 Hz), 3.67-3.74 (1H, m), 4.39 (1H, s), 6.47 (1H, s), 7.02 (1H, s), 7.10 (1H, t, J=8 Hz), 7.62 (1H, d, J=8 Hz), 9.31 (1H, s); ¹³C NMR (CDCl₃) δ=24.66, 25.37, 25.99, 32.43, 50.21, 106.53, 111.72, 120.70, 122.37, 129.50, 136.14, 154.03; ESI-MS: [M+H]⁺ calculated for $C_{16}H_{21}N_2O$: 257.3, found: 257.3.

Example 12

N-(4-methylcyclohexyl-1H-indole-2-carboxamide (mixture of isomers) (Compound 15)

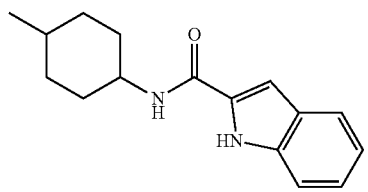 [SMILES: CC1CCC(NC(=O)c2cc3ccccc3[nH]2)CC1]

280 mg (54.6%) of white powder; $^1$H NMR (CDCl$_3$) δ=0.97 (3H, d, J=4 Hz), 1.23-1.29 (2H, m), 1.64-1.85 (7H, m), 4.27 (1H, s), 6.27 (1H, d, J=8 Hz), 6.85 (1H, s), 7.14 (1H, t, J=8 Hz), 7.28 (1H, t, J=8 Hz), 7.44 (1H, d, J=8 Hz), 7.64 (1H, d, J=8 Hz), 9.77 (1H, s); $^{13}$C NMR (CDCl$_3$) δ=21.13, 26.15, 29.41, 30.09, 30.48, 33.86, 45.80, 101.42, 112.05, 120.58, 121.77, 124.31, 127.66, 136.36, 160.96; ESI-MS: [M+H]$^+$ calculated for C$_{16}$H$_{21}$N$_2$O: 257.3, found: 256.9.

Example 13

N-((1R,2R,3R,5S)-2,6,6-trimethylbicyclo[3.1.1]heptan-3-yl)-1H-indole-2-carboxamide (Compound 16)

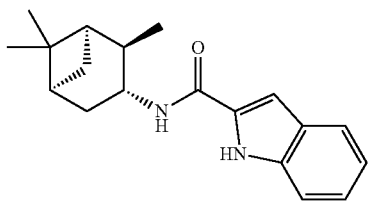 [SMILES: C[C@@H]1[C@H]2C[C@@H](C[C@H]1NC(=O)c1cc3ccccc3[nH]1)C2(C)C]

378 mg (63.8%) of white powder; $^1$H NMR (CDCl$_3$) δ=0.94 (1H, d, J=8 Hz), 1.13 (3H, s), 1.19 (3H, d, J=8 Hz), 1.27 (3H, s), 1.66-1.71 (1H, m), 1.88-1.98 (2H, m), 2.00-2.04 (1H, m), 2.45-2.51 (1H, m), 2.70-2.78 (1H, m), 4.55-4.63 (1H, m), 6.11 (1H, d, J=8 Hz), 6.86 (1H, d, J=4 Hz), 7.13 (1H, t, J=8 Hz), 7.27 (1H, t, J=8 Hz), 7.47 (1H, d, J=8 Hz), 7.63 (1H, d, J=8 Hz), 9.95 (1H, s); $^{13}$C NMR (CDCl$_3$) δ=20.83, 23.38, 28.05, 35.48, 38.50, 41.64, 46.49, 47.85, 48.21, 101.43, 112.12, 120.53, 121.77, 124.25, 127.65, 131.07, 136.45, 161.25; ESI-MS: [M+H]$^+$ calculated for C$_{19}$H$_{25}$N$_2$O: 297.4, found: 297.3.

Example 14

N-heptyl-1H-indole-2-carboxamide (Compound 17)

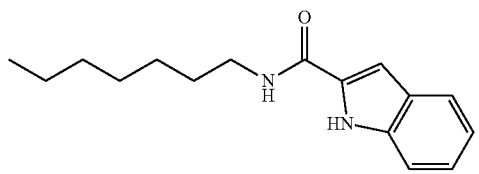 [SMILES: CCCCCCCNC(=O)c1cc2ccccc2[nH]1]

354 mg (68.5%) of white powder; $^1$H NMR (CDCl$_3$) δ=0.89 (3H, t, J=8 Hz), 1.28-1.41 (8H, m), 1.65 (2H, quin, J=8 Hz), 3.49 (2H, q, J=8 Hz), 6.19 (1H, s), 6.82 (1H, s), 7.14 (1H, t, J=8 Hz), 7.28 (1H, t, J=8 Hz), 7.43 (1H, d, J=8 Hz), 7.63 (1H, d, J=8 Hz), 9.56 (1H, s); $^{13}$C NMR (CDCl$_3$) δ=14.06, 22.60, 26.95, 28.99, 29.80, 31.76, 39.79, 101.51, 112.00, 120.61, 121.83, 124.38, 127.67, 130.91, 136.26, 161.63; ESI-MS: [M+H]$^+$ calculated for C$_{16}$H$_{23}$N$_2$O: 259.4, found: 259.1.

Example 15

N-octyl-1H-indole-2-carboxamide (Compound 18)

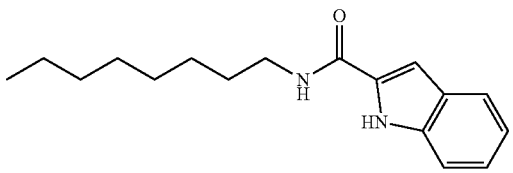 [SMILES: CCCCCCCCNC(=O)c1cc2ccccc2[nH]1]

267 mg (49.0%) of white powder; $^1$H NMR (CDCl$_3$) δ=0.88 (3H, t, J=8 Hz), 1.28-1.39 (10H, m), 1.64 (2H, quin, J=8 Hz), 3.48 (2H, q, J=8 Hz), 6.17 (1H, s), 6.81 (1H, s), 7.14 (1H, t, J=4 Hz), 7.28 (1H, t, J=8 Hz), 7.43 (1H, d, J=8 Hz), 7.63 (1H, d, J=8 Hz), 9.46 (1H, s); $^{13}$C NMR (CDCl$_3$) δ=14.09, 22.65, 26.99, 29.22, 29.79, 31.80, 39.79, 101.49, 111.97, 120.64, 121.84, 124.40, 127.88, 130.91, 136.22, 161.58; ESI-MS: [M+H]$^+$ calculated for C$_{17}$H$_{25}$N$_2$O: 273.3, found: 273.3.

Example 16

N-(3-chlorobenzyl)-1H-indole-2-carboxamide (Compound 19)

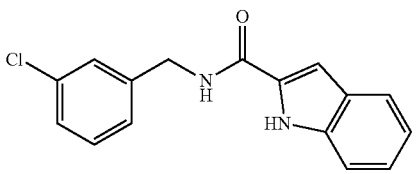 [SMILES: O=C(NCc1cccc(Cl)c1)c1cc2ccccc2[nH]1]

454 mg (79.7%) of white powder; $^1$H NMR (CDCl$_3$) δ=2.97 (2H, s), 4.61 (2H, s), 6.99 (1H, s), 7.12 (1H, t, J=4 Hz), 7.24-7.31 (4H, m), 7.35 (1H, s), 7.42 (1H, d, J=12 Hz), 7.63 (1H, d, J=8 Hz); $^{13}$C NMR (CDCl$_3$) δ=42.90, 48.92, 49.35, 49.57, 49.78, 103.21, 112.12, 120.60, 121.97, 124.61, 125.82, 127.71, 130.05, 134.59, 140.41, 162.27; ESI-MS: [M+H]$^+$ calculated for C$_{16}$H$_{14}$ClN$_2$O: 285.7, found: 285.0.

Example 17

General Synthetic Method for 4,6-Dimethyl-1H-Indole-2-Carboxamides

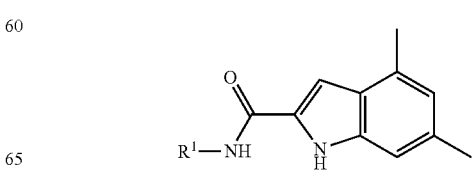

4,6-Dimethyl-1H-indole-2-carboxylic acid (Intermediate 2, 110 mg, 0.58 mmol) was combined with DMAP (0.4 mg, catalytic), DCC (180 mg, 0.87 mmol) and anhydrous $CH_2Cl_2$ (10 mL) and stirred. The amine (0.58 mmol) was added to mixture and allowed to stir overnight at room temperature. The formed precipitate was filtered and the filtrate solvent was removed by evaporation. Crude product was purified using flash column chromatography with a 0-40% EtAc in hexanes gradient.

Examples 18-32 were prepared according to the general procedures described in Example 17 using appropriately substituted starting materials.

Example 18

N-1-adamantyl-4,6-dimethyl-1H-indole-2-carboxamide (Compound 20)

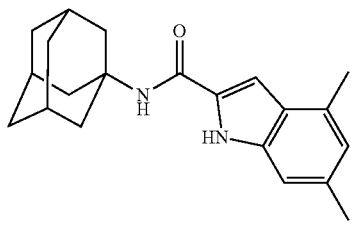 [SMILES: Cc1cc(C)c2cc(C(=O)NC34CC5CC(CC(C5)C3)C4)[nH]c2c1]

54 mg (31.0%) of white powder; $^1H$ NMR ($CDCl_3$) δ=1.75 (6H, s), 2.16 (9H, s), 2.42 (3H, s), 2.51 (3H, s), 5.85 (1H, s), 6.71 (1H, s), 6.77 (1H, s), 7.08 (1H, s), 9.23 (1H, s); $^{13}C$ NMR ($CDCl_3$) δ=18.62, 21.62, 29.52, 36.36, 41.90, 52.39, 99.67, 109.18, 122.67, 130.70, 130.86, 134.42, 136.39, 160.90; ESI-MS: $[M+H]^+$ calculated for $C_{21}H_{27}N_2O$: 323.4, found: 323.3.

Example 19

N-(3-ethyl-1-adamantyl)-4,6-dimethyl-1H-indole-2-carboxamide (Compound 21)

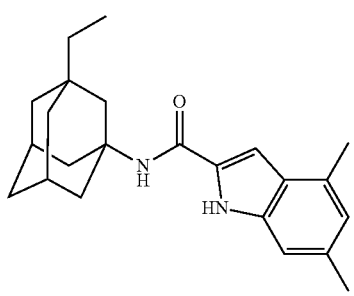 [SMILES: CCC12CC3CC(C1)CC(NC(=O)c1cc4c(C)cc(C)cc4[nH]1)(C3)C2]

61 mg (32.2%) of white powder; $^1H$ NMR ($CDCl_3$) δ=0.81 (3H, t, J=8 Hz), 1.20 (3H, q, J=8 Hz), 1.46 (4H, s), 1.56 (1H, s), 1.84 (1H, s), 2.06 (4H, q, J=12 Hz), 2.20 (3H, s), 2.42 (3H, s), 2.51 (3H, s), 5.85 (1H, s), 6.70 (1H, s), 6.77 (1H, s), 7.05 (1H, s), 9.02 (1H, s); $^{13}C$ NMR ($CDCl_3$) δ=7.05, 18.61, 21.62, 35.86, 40.79, 41.52, 46.23, 53.28, 99.68, 109.11, 122.72, 130.39, 134.49, 136.31, 160.89; ESI-MS: $[M+H]^+$ calculated for $C_{23}H_{31}N_2O$: 351.5, found: 351.7.

Example 20

N-(1-(1-adamantyl)ethyl)-4,6-dimethyl-1H-indole-2-carboxamide (Compound 22)

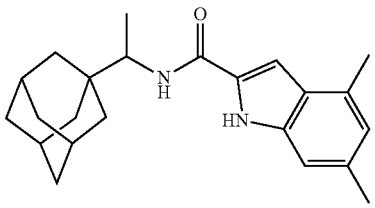 [SMILES: Cc1cc(C)c2cc(C(=O)NC(C)C34CC5CC(CC(C5)C3)C4)[nH]c2c1]

55 mg (29.1%) of white powder; $^1H$ NMR ($CDCl_3$) δ=1.16 (3H, d, J=4 Hz), 1.57-1.74 (14H, m), 2.02 (3H, s), 2.42 (3H, s), 2.53 (3H, s), 3.94-4.02 (1H, m), 5.98 (1H, d, J=8 Hz), 6.78 (2H, s), 7.06 (1H, s), 9.33 (1H, s); $^{13}C$ NMR ($CDCl_3$) δ=14.69, 18.64, 21.83, 28.3036.21, 37.01, 38.50, 53.08, 99.65, 109.17, 122.77, 125.65, 129.85, 130.86, 134.59, 136.47, 161.19; ESI-MS: $[M+H]^+$ calculated for $C_{23}H_{31}N_2O$: 351.5, found: 351.2.

Example 21

N-(1-(1-adamantyl)methyl)-4,6-dimethyl-1H-indole-2-carboxamide (Compound 23)

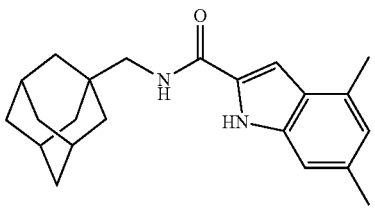 [SMILES: Cc1cc(C)c2cc(C(=O)NCC34CC5CC(CC(C5)C3)C4)[nH]c2c1]

62 mg (34.1%) of white powder; $^1H$ NMR ($CDCl_3$) δ=1.60 (6H, s), 1.64 (1H, s), 1.67 (2H, s), 1.72 (2H, s), 1.75 (1H, s), 2.01 (3H, s), 2.42 (3H, s), 2.52 (3H, s), 3.19 (2H, d, J=8 Hz), 6.24 (1H, s), 6.77 (1H, s), 6.81 (1H, s), 7.07 (1H, s), 9.53 (1H, s); $^{13}C$ NMR ($CDCl_3$) δ=18.62, 21.83, 28.22, 34.15, 36.90, 40.28, 50.97, 99.89, 109.18, 122.77, 125.67, 129.68, 130.90, 134.66, 136.49, 161.93; ESI-MS: $[M+H]^+$ calculated for $C_{22}H_{29}N_2O$: 337.4, found: 337.3.

Example 22

N-2-adamantyl-4,6-dimethyl-1H-indole-2-carboxamide (Compound 24)

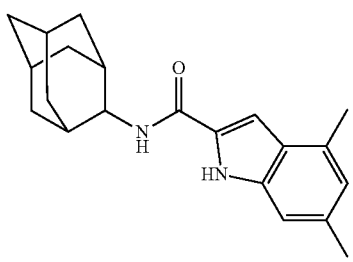 [SMILES: Cc1cc(C)c2cc(C(=O)NC3C4CC5CC(C4)CC3C5)[nH]c2c1]

83 mg (47.7%) of white powder; $^1$H NMR (CDCl$_3$) δ=1.72 (1H, s), 1.75 (1H, s), 1.80 (2H, s), 1.93 (8H, s), 2.52 (4H, s), 2.52 (4H, s), 4.34 (1H, d, J=8 Hz), 6.51 (1H, d, J=8 Hz), 6.76 (2H, d, J=20 Hz), 7.09 (1H, s), 10.01 (1H, s); $^{13}$C NMR (CDCl$_3$) δ=18.58, 18.66, 21.87, 27.28, 32.07, 37.23, 37.53, 53.66, 99.90, 109.37, 109.46, 110.91, 122.65, 123.53, 130.79, 134.42, 136.88, 137.44, 138.86, 157.48, 161.21; ESI-MS: [M+H]$^+$ calculated for C$_{21}$H$_{27}$N$_2$O: 323.4, found: 323.3.

Example 23

N-cyclooctyl-4,6-dimethyl-1H-indole-2-carboxamide (Compound 25)

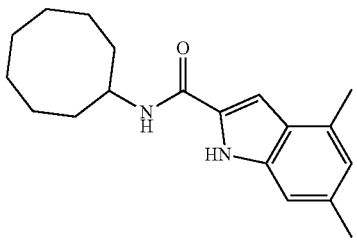 [SMILES: Cc1cc(C)c2cc(C(=O)NC3CCCCCCC3)[nH]c2c1]

56 mg (34.8%) of white powder; $^1$H NMR (CDCl$_3$) δ=1.57-1.75 (14H, m), 1.93-2.01 (2H, m), 2.42 (3H, s), 2.51 (3H, s), 4.21-4.30 (1H, m), 6.09 (1H, d, J=8 Hz), 6.77 (2H, s), 7.07 (1H, s), 9.44 (1H, s); $^{13}$C NMR (CDCl$_3$) δ=18.62, 21.83, 23.79, 27.19, 32.55, 49.63, 99.92, 109.23, 122.71, 125.71, 130.88, 134.53, 136.55, 160.65; ESI-MS: [M+H]$^+$ calculated for C$_{19}$H$_{27}$N$_2$O: 299.4, found: 299.0.

Example 24

N-cycloheptyl-4,6-dimethyl-1H-indole-2-carboxamide (Compound 26)

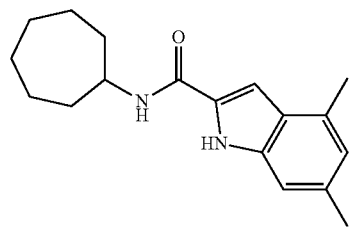 [SMILES: Cc1cc(C)c2cc(C(=O)NC3CCCCCC3)[nH]c2c1]

65 mg (42.3%) of white powder; $^1$H NMR (CDCl$_3$) δ=1.56-1.59 (6H, m), 1.61-1.73 (4H, m), 2.04-2.09 (2H, m), 2.42 (3H, s), 2.51 (3H, s), 4.19 (1H, s), 6.06 (1H, d, J=8 Hz), 6.77 (2H, s), 7.06 (1H, s), 9.25 (1H, s); $^{13}$C NMR (CDCl$_3$) δ=18.62, 21.84, 24.17, 28.06, 31.03, 35.32, 50.68, 99.90, 109.17, 122.75, 125.72, 130.92, 134.59, 136.46, 160.61; ESI-MS: [M+H]$^+$ calculated for C$_{18}$H$_{25}$N$_2$O: 285.4, found: 285.3.

Example 25

N-cyclohexyl-4,6-dimethyl-1H-indole-2-carboxamide (Compound 27)

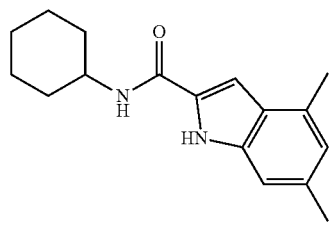 [SMILES: Cc1cc(C)c2cc(C(=O)NC3CCCCC3)[nH]c2c1]

69 mg (47.3%) of white powder; $^1$H NMR (CDCl$_3$) δ=0.83-0.90 (1H, m), 1.21-1.32 (6H, m), 1.56 (2H, s), 1.75-1.80 (2H, m), 1.91 (2H, m), 2.03 (1H, d, J=16 Hz), 2.43 (2H, s), 2.48 (2H, s), 6.77 (2H, d, J=4 Hz), 7.05 (1H, s), 9.01 (1H, s); $^{13}$C NMR (CDCl$_3$) δ=18.62, 24.95, 25.57, 33.38, 34.94, 48.44, 99.94, 109.09, 122.80, 130.98, 134.68; ESI-MS: [M+H]$^+$ calculated for C$_{17}$H$_{23}$N$_2$O: 271.3, found: 271.2.

Example 26

N-cyclopentyl-4,6-dimethyl-1H-indole-2-carboxamide (Compound 28)

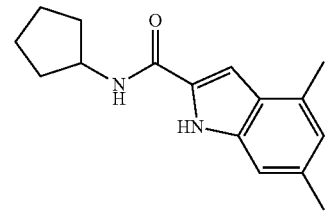 [SMILES: Cc1cc(C)c2cc(C(=O)NC3CCCC3)[nH]c2c1]

72 mg (52.0%) of white powder; $^1$H NMR (CDCl$_3$) δ=1.55 (2H, quin, J=8 Hz), 1.63-1.79 (4H, m), 2.08-2.12 (2H, m), 2.42 (3H, s), 2.50 (3H, s), 4.44 (1H, q, J=8 Hz), 6.11 (1H, d, J=8 Hz), 6.77-6.79 (2H, m), 7.05 (1H, s), 9.39 (1H, s); $^{13}$C NMR (CDCl$_3$) δ=18.61, 21.85, 33.32, 51.43, 100.11, 109.23, 122.72, 125.71, 134.60, 136.55, 161.46; ESI-MS: [M+H]$^+$ calculated for C$_{16}$H$_{21}$N$_2$O: 257.3, found: 257.1.

Example 27

4,6-dimethyl-N-((1s,4s)-4-methylcyclohexyl)-1H-indole-2-carboxamide (Compound 29)

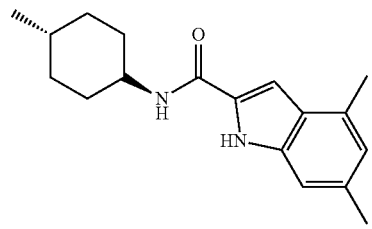

77 mg (50.1%) of white powder; $^1$H NMR (CDCl$_3$) δ=0.92 (2H, d, J=8 Hz), 1.08-1.27 (6H, m), 1.60 (1H, s), 1.75 (1H, d, J=16 Hz), 1.92 (2H, d, J=16 Hz), 2.08 (1H, d, J=12 Hz), 2.42 (3H, s), 2.51 (3H, s), 5.93 (1H, d, J=8 Hz), 6.77 (2H, s), 7.05 (1H, s), 9.18 (1H, s); $^{13}$C NMR (CDCl$_3$) δ=18.61, 21.84, 22.19, 32.01, 33.88, 34.93, 48.73, 99.98, 109.14, 122.75, 125.73, 130.94, 134.63, 136.43, 160.92; ESI-MS: [M+H]$^+$ calculated for C$_{18}$H$_{25}$N$_2$O: 285.4, found: 285.3.

Example 28

N-4-methylcyclohexyl-4,6-dimethyl-1H-indole-2-carboxamide (Mixture of Isomers) (Compound 30)

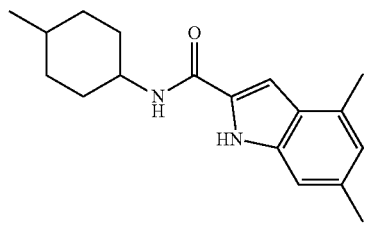

80 mg (52.1%) of white powder; $^1$H NMR (CDCl$_3$) δ=0.92 (1H, d, J=4 Hz), 0.97 (1H, d, J=8 Hz), 1.11-1.28 (4H, m), 1.65-1.80 (6H, m), 2.10 (1H, d, J=12 Hz), 2.42-2.52 (6H, m), 6.02-6.27 (1H, m), 6.76-6.80 (2H, m), 7.06 (1H, s), 9.63 (1H, d, J=16 Hz); $^{13}$C NMR (CDCl$_3$) δ=18.62, 18.66, 21.95, 22.20, 29.40, 30.14, 33.92, 45.84, 48.82, 99.97, 100.06, 109.30, 122.70, 125.68, 130.67, 136.66, 161.14; ESI-MS: [M+H]$^+$ calculated for C$_{18}$H$_{25}$N$_2$O: 285.3, found: 285.3.

Example 29

N-((1R,2R,3R,5S)-2,6,6-trimethylbicyclo[3.1.1]heptan-3-yl)-4,6-dimethyl-1H-indole-2-carboxamide (Compound 31)

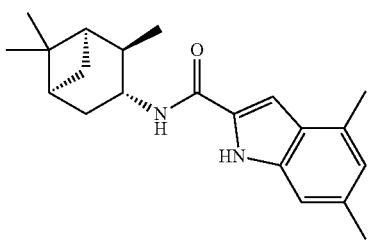

60 mg (34.2%) of white powder; $^1$H NMR (CDCl$_3$) δ=0.96 (1H, d, J=8 Hz), 1.14 (3H, s), 1.19 (3H, d, J=8 Hz), 1.27 (3H, s), 1.66-1.72 (1H, m), 1.88-1.97 (2H, m), 2.03 (1H, s), 2.42 (3H, s), 2.45-2.50 (1H, m), 2.52 (3H, s), 2.70-2.77 (1H, m), 2.88 (1H, d, J=28 Hz), 4.57 (1H, t, J=16 Hz), 6.06 (1H, d, J=8 Hz), 6.77 (1H, s), 6.82 (1H, s), 7.10 (1H, s), 9.66 (1H, s); $^{13}$C NMR (CDCl$_3$) δ=18.64, 20.86, 21.83, 23.48, 28.05, 37.42, 38.52, 41.66, 46.54, 47.87, 48.10, 99.98, 10933, 122.70, 125.71, 130.86, 134.52, 136.70, 161.34; ESI-MS: [M+H]$^+$ calculated for C$_{21}$H$_{29}$N$_2$O: 325.4, found: 325.1.

Example 30

N-heptyl-4,6-dimethyl-1H-indole-2-carboxamide (Compound 32)

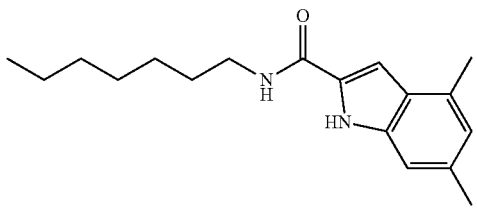 [SMILES: CCCCCCCNC(=O)c1cc2c(C)cc(C)cc2[nH]1]

99 mg (64.0%) of white powder; $^1$H NMR (CDCl$_3$) δ=0.88 (3H, t, J=4 Hz), 1.28-1.39 (7H, m), 1.64 (3H, quin, J=8 Hz), 1.92-1.95 (1H, m), 2.42 (2H, s), 2.47 (1H, s), 2.50 (3H, s), 3.47 (2H, q, J=8 Hz), 6.19 (1H, s), 6.77 (2H, d, J=8 Hz), 7.05 (1H, s), 9.38 (1H, s); $^{13}$C NMR (CDCl$_3$) δ=14.07, 18.81, 21.84, 22.61, 26.98, 29.02, 31.76, 39.75, 100.14, 109.21, 122.75, 129.71, 130.93, 134.64, 136.54, 161.79; ESI-MS: [M+H]$^+$ calculated for C$_{18}$H$_{27}$N$_2$O: 287.4, found: 287.3.

Example 31

N-octyl-4,6-dimethyl-1H-indole-2-carboxamide (Compound 33)

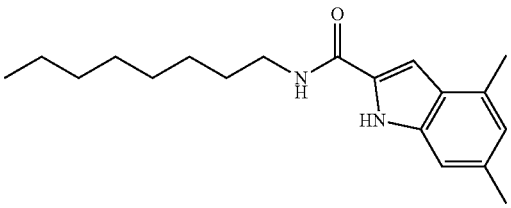 [SMILES: CCCCCCCCNC(=O)c1cc2c(C)cc(C)cc2[nH]1]

101 mg (62.3%) of white powder; $^1$H NMR (CDCl$_3$) δ=0.88 (3H, t, J=8 Hz), 1.28-1.37 (9H, m), 1.62-1.65 (3H, m), 2.42 (3H, s), 2.50 (3H, s), 3.47 (2H, q, J=8 Hz), 6.16 (1H, s), 6.77 (2H, d, J=4 Hz), 7.05 (1H, s), 9.27 (1H, s); $^{13}$C NMR (CDCl$_3$) δ=14.09, 18.60, 22.65, 27.02, 29.23, 29.85, 31.81, 37.75, 100.13, 109.19, 122.77, 125.73, 130.94, 134.68, 136.52, 161.77; ESI-MS: [M+H]$^+$ calculated for C$_{19}$H$_{29}$N$_2$O: 301.4, found: 301.4.

Example 32

N-(3-chlorobenzyl)-4,6-dimethyl-1H-indole-2-carboxamide (Compound 34)

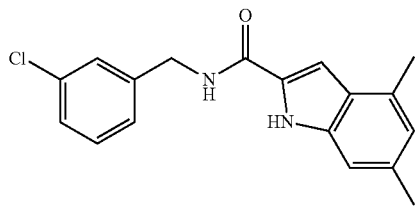 [SMILES: Cc1cc(C)c2cc(C(=O)NCc3cccc(Cl)c3)[nH]c2c1]

103 mg (61.0%) of white powder; $^1$H NMR (CDCl$_3$) δ=1.58 (1H, s), 1.75 (6H, t, J=12 Hz), 2.16 (8H, s), 2.42 (3H, s), 2.51 (3H, s), 5.85 (1H, s), 6.71 (1H, s), 6.77 (1H, s), 7.08 (1H, s), 9.23 (1H, s); $^{13}$C NMR (CDCl$_3$) δ=18.62, 21.82, 29.52, 36.36, 41.90, 52.39, 99.67, 109.18, 122.67, 130.86, 134.42, 136.39, 160.90; ESI-MS: [M+H]$^P$ calculated for C$_{18}$H$_{18}$ClN$_2$O: 313.7, found: 313.2.

Example 33

Inhibitor Susceptibility Assays

MIC values against a number of clinical isolates of mycobacteria and other bacterial species were determined in 96-well microtiter plates using the colorimetric resazurin microtiter assay (see e.g., Martin et al, *Antimicrob. Agents Chemother.* 2003, 47:3616-3619) and visually scanning for growth. MIC values against *M. tuberculosis* H37Rv mc$^2$6206 were determined in 7H9-ADC-0.05% tyloxapol medium supplemented with 0.2% casaminoacids, 48 μg/mL pantothenate and 50 μg/mL L-leucine. MICs against *M. smegmatis* mc$^2$155 were determined in 7H9-ADC-0.05% Tween 80. MICs against *M. abscessus* ATCC 19977, *M. abscessus* 21, *M. abscessus* 103, *M. massiliense* CIP108297, *M. massiliense* 1513, *M. massiliense* CRM-0019, *M. massiliense* CRM-0270, *M. massiliense* 105, *M. bolletii* ATCC 14472, *M. bolletii* 88, *M. chelonae* ATCC 35752, *M. chelonae* 28, *M. chelonae* 49, *M. chelonae* 69, *M. kansasii* 662, *M. avium* 104, *M. intracellulare* 1956, *M. xenopi* 4042, *Pseudomonas aeruginosa* PAO-1 and *Staphylococcus aureus* ATCC 25923 were determined in Mueller Hinton II (BD). MBC$_{90}$ values were determined by subculture from the MIC wells onto 7H11 agar and defined as the lowest concentration reducing CFU by 90% relative to the inoculum.

Table 1 shows the minimum inhibitory concentration (MIC) values for the synthesized unsubstituted IC compounds (MIC values reported in μg/mL). Overall, these compounds had limited pan-antimycobacterial activity as demonstrated by inhibition from compounds 5 and 16. Excluding *M. smegmatis*, compounds 5 and 16 show the best antimycobacterial activity with sub-μg/mL MIC values and compound 16 obtaining 2-4-fold increased activity over 5. An adamantyl substitution in compound 5 conferred activity, however the 3-ethyl adamantyl (6) or adamantyl with an ethyl or methyl linker (7, 8) was less tolerated. Interestingly, changing the connection point from the 1-position (5) to the 2-position (9) on adamantine abolished anti-NTM activity, however potent activity was retained against *M. tuberculosis*. The methyl-linked adamantyl substitution on compound 8 elicited greater activity against NTM than the larger ethyl-linked compound 7, suggesting an upper limit for linker bulk. Saturated cycloalkyl rings that are 8 carbons or smaller (10, 11, 12, and 13) abolished all anti-NTM activity. However, adding methyl components to smaller aliphatic rings can increase activity as seen with the isopinocampheyl substituted (16), which attained the highest pan-activity of the series.

The antitubercular SAR was much looser, as the constraints on for the bulky aliphatic group are less restrictive. A cyclooctyl (10) substituent maintained antimicrobial activity against *M. tuberculosis* with an MIC of 0.39 μg/mL, despite being absent for NTM species. However, smaller rings like cycloheptyl, cyclohexyl, and cyclopentyl (11, 12, and 13) are not tolerated for any species. There remained modest anti-TB activity with the 3-ethyl adamantyl (6) with an MIC of 1.25 μg/mL.

TABLE 1

| Compound # | *M. abscessus* ATCC 19977 | *M. abscessus* DCI #21 | *M. massiliense* CIP 108297 | *M. massiliense* CRM 0019 | *M. bolletii* ATCC 14472 | *M. chelonae* ATCC 35752 | *M. tb* H37 Rv (mc2-6206) | *M. smeg.* mc$^2$155 |
|---|---|---|---|---|---|---|---|---|
| 5  | 0.25 | 0.25 | 0.5  | 0.25 | 0.25 | 0.25   | 0.2  | 1.56 |
| 6  | >32  | >32  | >32  | >32  | >32  | >32    | 1.25 | >20  |
| 7  | 16   | 16   | 8    | 8    | 16   | 2      | >5   | >20  |
| 8  | 2    | 2    | 2    | >32  | 2    | 1      | >5   | >20  |
| 9  | >32  | >32  | >32  | 32   | 32   | >32    | 0.39 | >25  |
| 10 | >32  | >32  | >32  | 32   | 32   | >32    | 0.39 | 25   |
| 11 | >32  | >32  | >32  | >32  | >32  | >32    | >5   | >20  |
| 12 | >32  | >32  | >32  | >32  | >32  | >32    | >10  | >25  |
| 13 | >32  | >32  | >32  | >32  | >32  | >32    | >10  | >25  |
| 14 | >32  | >32  | >32  | >32  | >32  | >32    | >10  | >25  |
| 15 | >32  | >32  | 16   | 16   | 16   | 16     | 5    | 12.5 |
| 16 | 0.12 | 0.5  | 0.06 | 0.06 | 0.12 | <0.06  | 0.05 | 0.78 |
| 17 | >32  | >32  | >32  | >32  | >32  | >32    | >10  | >25  |
| 18 | >32  | >32  | >32  | >32  | >32  | >32    | >10  | >25  |
| 19 | >32  | >32  | >32  | >32  | >32  | >32    | >5   | >20  |

The second series evaluated for pan-antimycobacterial activity was the 4,6-dimethyl indole substitution, and this substitution pattern contributed to greater potency against the mycobacterial panel than with the unsubstituted indole compounds as demonstrated in Table 2 (MIC values reported in μg/mL). The most potent pan-activity was observed with cyclooctyl (25) and cycloheptyl (26) head groups with MIC values ranging from 0.0039 to 0.625 m/mL, depending on the species of *Mycobacterium*. The 4-methylcyclohexyl substituted compounds (29 and 30) also displayed significant anti-NTM and anti-TB activity with the exception of *M. smegmatis*. The pure trans isomer (29) and cis/trans mixture (30) achieved the same MIC values showing no preference for stereochemical orientation at the 4-position. The dimethyl indole series allowed for smaller aliphatic substituents, presumably through the maintaining of lipophilicity from the dimethyl groups. Aliphatic rings smaller than cyclooctyl conferred anti-mycobacterial activity that was not present in the unsubstituted indoles 11, 12, 13 and 14. Substituents the size of the cyclooctyl (25) or cycloheptyl (26) had activity against *M. abscessus, M. massiliense, M. bolletii, M. chelonae, M. smegmatis,* and *M. tuberculosis* but began to lose potency as the ring size decreases, until any clinically relevant activity is lost at a size of a cyclopentyl (28). Compounds with substitutions larger than adamantyl (20, 21, 22, 23) lost all anti-MAB SC NTM activity. Comparable to the unsubstituted indoles of Table 1, activity against *M. tuberculosis* in the dimethyl series was less sensitive to substituent size than that of NTM species. The majority of these compounds (20, 21, 22, 23, 24, 25, 26, 27, 29, 30, and 31) exhibited anti-tuberculous activity with MIC values ranging from 0.00195 to 0.625 µg/mL.

TABLE 2

| Compound # | M. abscessus ATCC 19977 | M. abscessus DCI #21 | M. massiliense CIP 108297 | M. massiliense CRM 0019 | M. bolletii ATCC 14472 | M. chelonae ATCC 35752 | M. tb H37 Rv (mc2-6206) | M. smeg. mc²155 |
|---|---|---|---|---|---|---|---|---|
| 20 | >32 | 32 | >32 | >32 | >32 | >32 | 0.0195 | 1.25-2.50 |
| 21 | >32 | >32 | >32 | >32 | >32 | >32 | 0.039 | >20 |
| 22 | 16 | >32 | 8 | 8 | 16 | 16 | 0.31 | >20 |
| 23 | >32 | >32 | >32 | >32 | >32 | >32 | 0.16 | >20 |
| 24 | >32 | >32 | >32 | >32 | >32 | >32 | 0.04 | >20 |
| 25 | 0.063 | 0.0078 | 0.031 | 0.0078 | 0.0039 | 0.063 | 0.0195 | 0.313-0.625 |
| 26 | ≤0.06 | ≤0.06 | ≤0.06 | ≤0.06 | ≤0.06 | ≤0.06 | 0.08 | 0.625 |
| 27 | 0.5 | 0.25 | 0.25 | 0.25 | 0.25 | 0.25 | 0.625 | 2.5 |
| 28 | 4 | 4 | 8 | 8 | 2 | 2 | 2.5 | 5 |
| 29 | ≤0.06 | ≤0.06 | ≤0.06 | ≤0.06 | ≤0.06 | ≤0.06 | 0.31 | >20 |
| 30 | ≤0.06 | ≤0.06 | ≤0.06 | ≤0.06 | ≤0.06 | ≤0.06 | 0.31 | >20 |
| 31 | 0.125 | 0.125 | 0.125 | 0.125 | 0.125 | 0.125 | 0.0195 | 1.25-2.50 |
| 32 | >32 | >32 | >32 | >32 | 32 | >32 | >5 | 5 |
| 33 | >32 | >32 | >32 | >32 | >32 | >32 | >20 | 2.50-5.00 |
| 34 | >32 | >32 | >32 | >32 | >32 | >32 | >5 | >20 |

Regarding the unsubstituted ICs, only two compounds demonstrated sub-µg/mL pan-activity potencies compared to six dimethyl ICs. Furthermore, preference for bulky aliphatic rings is shown, since potency was lost with decreasing ring size in both series, albeit more drastically in the unsubstituted series. It was clearly seen that the 4,6-dimethylated indole is preferred due to the acquisition of previously absent anti-mycobacterial activity (25, 26-29), which is most likely due to the boost in lipophilicity from the two methyl groups. Supporting this observation was the attainment of anti-NTM activity for smaller saturated cycloalkyl substitutions (Table 2, compounds 25, 26, 27, 29, and 30) when the indole ring was dimethylated. The anti-NTM activity seen with adamantyl (Table 1, 5) in the unsubstituted ICs was abolished when the indole was 4,6-dimethylated (Table 2, 20), however, this was not the case for the isopinocampheyl substitution in either series (Table 1, 16 and Table 2, 31). It seems when this minimum liphophilic threshold is not met, such as with the aliphatic rings smaller than an 8-carbon ring size in the unsubstituted series (Table 1, 10, 11, 12, and 13), the compounds suffered a loss of activity. Lastly, no anti-mycobacterial activity was observed in either series for uncyclized straight alkyl chains (Table 1, compounds 17, 18; table 2, compounds 32, 33).

The compounds were also tested against MAC strains including *M. avium* and *M. xenopi* to further evaluate the spectrum of anti-mycobacterial activity of the IC compounds, (Table 3; MIC values reported in µg/mL). Compounds that were not effective anti-mycobacterial agents were not tested. Overall, current IC compounds were more active against *M. xenopi* over *M. avium*. The best potential candidate for pan-activity against mycobacteria was the cyclooctyl substituted 4,6-dimethyl-indole (25), which also showed the most potent activity in this panel with MIC values ranging from 0.25-1 µg/mL. Compounds 26 and 31 also showed good activity against *M. avium* in addition to *M. xenopi* with MIC values between 2-4 µg/mL.

TABLE 3

| Compound # | M. avium 104 | M. avium Intracellulare 1956 | M. xenopi WT |
|---|---|---|---|
| 5 | 8 | 8 | 0.5-1.0 |
| 6 | >32 | >32 | 1.0-2.0 |

TABLE 3-continued

| Compound # | M. avium 104 | M. avium Intracellulare 1956 | M. xenopi WT |
|---|---|---|---|
| 7 | >32 | 32 | 8 |
| 8 | >32 | >32 | 4 |
| 9 | >32 | >32 | 2 |
| 10 | >32 | >32 | 2 |
| 15 | >32 | >32 | 16 |
| 16 | 8 | 8 | 0.5-1.0 |
| 20 | >32 | >32 | >32 |
| 21 | >32 | >32 | >32 |
| 22 | >32 | >32 | >32 |
| 23 | >32 | >32 | 1 |
| 24 | >32 | >32 | 0.5-1.0 |
| 25 | 0.25-0.05 | 1 | 0.25 |
| 26 | 2 | 4 | 0.06-0.12 |
| 27 | >32 | >32 | 1.0-2.0 |
| 28 | >32 | >32 | 8-16 |
| 29 | >32 | >32 | 0.25-1 |
| 30 | >32 | >32 | 0.5-1 |
| 31 | 2 | 2 | 0.25-1 |
| 32 | >32 | >32 | >32 |
| 33 | >32 | >32 | >32 |

Lead compounds in this IC series appeared to be selective for mycobacteria, as IC compounds 5, 16, 25, 26, 30 and 31 were inactive against *P. aeruginosa* and *S. aureus* (Table 4). All compounds tested showed no bacterial growth inhibition up to 160 µg/mL, except for 16, which inhibited *S. aureus* growth at 40 µg/mL.

TABLE 4

| Compound # | MIC (µg/mL) P. aeruginosa PAO-1 | MIC (µg/mL) S. aureus ATCC25923 |
|---|---|---|
| 5 | >160 | >160 |
| 16 | >160 | 40 |
| 25 | >160 | >160 |
| 26 | >160 | >160 |

TABLE 4-continued

| | MIC (μg/mL) | |
|---|---|---|
| Compound # | P. aeruginosa PAO-1 | S. aureus ATCC25923 |
| 30 | >160 | >160 |
| 31 | >160 | >160 |

Minimum bactericidal concentration (MBC) values were determined for IC compounds 16, 25, 26 and 30. For these tested IC compounds, $MBC_{90}$ values were highly potent and similar to determined MIC values. $MBC_{90}$ values for IC 16, 25, 26, and 30 were 0.06, 0.015, 0.015 and 0.03 μg/mL, respectively.

Example 34

Cytotoxicity Assays

The cytotoxicity of compounds was determined by measuring THP-1 cell viability after 3 days in the presence of test compounds. Compounds were prepared as 10-point serial dilutions in DMSO. The highest concentration of compound tested was 50 μM where compounds were soluble in DMSO at 10 mM. THP-1 cells were cultured in complete RPMI and differentiated into macrophage-like cells using 80 nM PMA overnight at 37° C., 5% $CO_2$. Cells were inoculated into assay plates and cultured for 24 h before compound dilutions were added to a final DMSO concentration of 0.5%. Each run included staurosporine as a control. Assay plates were incubated for 3 days at 37° C., 5% $CO_2$, growth was measured using the CellTiter-Glo® Luminescent Cell Viability Assay (Promega) which uses ATP as an indicator of cell viability. Relative luminescent units (RLU) were measured using a Biotek Synergy 4 plate reader. The dose response curve was fitted using the Levenberg-Marquardt algorithm. The $IC_{50}$ was defined as the compound concentration that resulted in 50% viability.

The cytotoxicity of compounds 5, 16, 25, and 31 was tested against THP-1 cells, a human cell line (Table 5). With the exception of Compound 16 ($TD_{50}$ of 11.3 μg/mL), the ICs were found not to be cytotoxic up to 50 μM. Across several Mycobacterium species, these compounds have exceptional selectivity indices, ranging from 22.6 to at least 3,800. Compound 25, the most potent of the scaffold, shows the most promise against NTM, with selectivity indices of >1,910 for M. abscessus, M. massiliense, and M. bolleti, while compound 31 holds the most selectivity against M. tuberculosis.

concentrations of inhibitors for 16 hr at 37° C. with shaking. 0.5 μCi/mL [1,2-$^{14}$C]acetic acid (specific activity, 52 Ci/mol, PerkinElmer Inc.) was added at the same time as the inhibitors. Total lipids and cell wall-bound mycolic acid methyl esters were prepared from treated and untreated cells and analyzed by TLC as described in Grzegorzewicz et al, Nature Chemical Biology, 2012, 8:334+341. TLCs were revealed and semi-quantified using a Phosphorlmager (Typhoon, GE Healthcare).

IC compounds, including compound 5, have been reported to target the M. tuberculosis trehalose monomycolate (TMM) transporter, MmpL3, resulting in an inhibition of the transfer of mycolic acids to their cell envelope acceptors, arabinogalactan and trehalose dimycolates (TDM).[29,31,36] To determine whether the NTM inhibitors identified herein displayed a similar activity on M. abscessus complex strains, cultures of M. massiliense strain 1513 treated with different concentrations of compounds 5, 16, 25 and 31 were metabolically labeled with [1,2-$^{14}$C]acetate and their lipid and cell wall-bound mycolic acid contents analyzed by TLC. Inhibitor treatments resulted in a concentration-dependent build-up of TMM in the cells that accompanied a decrease in mycolic acid transfer onto cell wall arabinogalactan and TDM (FIGS. 1A-1B). Inhibitor concentration-dependence was less marked in the case of compound 5. Thus, similar to the situation in M. tuberculosis, the IC described herein did not inhibit mycolic acid biosynthesis per se but rather the transfer of these products to their cell envelope acceptors. It is likely that the killing of M. abscessus complex strains that ensues results from the inhibition of the formation of their outer membrane.

Example 36

Activity of Indole-2-Carboximides Against M. abscessus

MIC testing was performed by microbroth dilution method using Mueller Hinton (MH) broth (Cation Adjusted) to the calcium and magnesium ion concentration recommended in the CLSI standard M7-A7 (Becton Dickinson). MIC testing also was performed by microbroth dilution method using 7H9 broth (Sigma-Aldrich). The justification for use of both MH and 7H9 broth for compound screening is anti-mycobacterial compounds can display different MIC activity depending on the broth that is used in the MIC assay. Rapid growing NTMs were grown on 7H11 agar plates (Sigma-Aldrich) for 3 days at 35-37° C. in ambient air (depending on bacterial strain). Slow growing (SG) NTMs

TABLE 5

| | | Selectivity Indices ($TD_{50}$/MIC) | | | | |
|---|---|---|---|---|---|---|
| Compound | $TD_{50}$ (μg/mL) | M. abscessus DCI #21 | M. Massiliense CRM0019 | M. bolletii | M. Chelonae ATCC14472 | M. tb H37Rv |
| 5 | >14.7 | >58 | >58 | >58 | >58 | >73 |
| 16 | 11.3 | 22.6 | 188 | 92 | >188 | 226 |
| 25 | >14.9 | >1910 | >1910 | >3820 | >236 | >764 |
| 31 | >16.2 | >130 | >130 | >130 | >130 | >830 |

Example 35

Metabolic Labeling and Mycolic Acid Analysis

Cultures of M. massiliense 1513 grown to mid log-phase in Mueller-Hinton II broth were incubated with different were grown on agar 7H11 plates (Sigma-Aldrich) for 21-30 days at 37° C. in ambient air. The CFUs were taken from the agar plates and placed in either MH or 7H9 broth with 0.05% Tween-80 and grown at 35-37° C. in ambient air until the optical density (OD) absorbance taken after 3 days (RGM) or 12 (SG) of growth had an (OD) 0.08-0.1 (0.5 McFarland Standard). The bacterial cell suspensions were then confirmed by preparing them in saline, matching the (OD) 0.08-0.1 (0.5 McFarland Standard). The broth (MH or 7H9) 180 μL was added to the first column in the 96-well plates. Then 100 μl of the broth (MH or 7H9) was added to the other columns in the 96 well plate. Compounds solutions were prepared at 1.28 mg/mL in DMSO (supplier recommended) and used immediately in the test range of 64-0.062 m/mL; 20 μL of compound was added to the first column of wells and 100 μl was serially diluted. Finally, 100 μl of NTM cell suspension was added in all the wells except the media only control wells. QC agents specific for each organism were assayed, including 1) a bacteria only negative control; 2) a media only negative control; 3) a (CLA) clarithromycin positive drug control; and 4) an optional E. coli control. RGMs were assayed for ODs on day 3, and SL on day 12. After that, the plate was assayed by using the Resazurin Microtiter Assay Plate method as recommended by the Clinical and Laboratories Standards Institute. Briefly, the method uses the addition of resazurin (7-Hydroxy-3H-phenoxazin-3-one 10-oxide) to the MIC 96 well plate. Resazurin is a blue dye, itself weakly fluorescent until it is irreversibly reduced to the pink colored and highly red fluorescent resorufin.

The indolecarboxamides series of compounds 5, 16, 25, and 31 all demonstrated MICs of 16 μg/mL (MH broth) comparable to the positive control of clarithromycin (MIC of 16 μg/mL (7H9) and 4 μg/mL (MH)) and amikacin (MIC 8 μg/mL (7H9) and 4 μg/mL (MH)) against M. abscessus subsp. bolletii 103, as shown in Table 6. Respectively, both compounds 5 and 25 demonstrated increased activity with an MIC of 32 μg/mL (MH) and MIC of 16 μg/mL (MH) compared to the positive controls clarithromycin (MIC of >64 μg/mL (7H9) and >64 μg/mL (MH)) and amikacin (MIC>64 μg/mL (7H9) and >64 μg/mL (MH)) against M. abscessus subsp. abscessus 1513.

TABLE 6

|  | M. abscessus 103 | | M. abscessus 1513 | |
| --- | --- | --- | --- | --- |
| Compound | 7H9 Broth | MH Broth | 7H9 Broth | MH Broth |
| 5 | >64 | 16 | >64 | 32 |
| 16 | >64 | 16 | >64 | >64 |
| 31 | >64 | 16 | >64 | >64 |
| 25 | >64 | 16 | >64 | 16 |

The indolecarboxamide compound 25 demonstrated a $MBC_{99}$ of 64 μg/mL (MH broth) compared to the positive controls amikacin ($MBC_{99}$>64 μg/mL (7H9 and MH)) and clarithromycin ($MBC_{99}$>64 μg/mL (7H9 and MH)) against M. abscessus subsp. bolletii 103 and M. abscessus subsp. abscessus 1513.

Example 37

In Vivo Acute Toxicity Assay 6-8 week old Balb/C female mice were ordered from Charles River. Mice were rested one to two weeks before dosing. For each dose of compound, 3 mice were utilized. Mice will be dosed at 40, 75 and 100 mg/kg. Compound was given twice per day for 3 consecutive days by gavage, at 100 μl/mouse. Compounds were prepared the day before or the day of dosing and stored at 4° C. until dosing. The time of dosing was recorded for each mouse. Observations were recorded immediately, at 10 min, 1 hour, 2 hours, 4 hours, and 24 hours after dosing. Any animals that showed signs of toxicity were euthanized in accordance with Colorado State University IACUC guidelines. Mice were dosed for three days and on the fourth day mice were observed twice daily for two days, then once daily for five days. In case the compound was found to show any adverse effects, a second multiple-day MTD model was performed using a lower concentration range of the experimental compound.

As an initial in vivo study, the safety of compounds and preliminary pharmacokinetics was assessed in an acute toxicity mouse model (Maximum Tolerated Dose assay, MTD) to evaluate any potential adverse effects and determine a safe dose for mouse efficacy studies. Compounds were tested to ensure safe use in healthy mice prior to any further in vivo testing. In this acute toxicity test, three healthy mice were given three consecutive daily doses of the compound and were observed at regular times for any adverse effects. Novel compounds were generally administered to mice at 40, 75 and 100 mg/kg in a tested formulation, administered on three consecutive days, 3 mice per dose group, in the chosen formulation. Doses higher than 300 mg/kg generally showed insolubility issues. Mice were observed 10 min, 1, 2, 4 hours after dosing and then daily afterwards. During the observations, humane handling practices and animal welfare regulations were strictly followed. In case the compound was found to show any adverse effects, a second multiple-day MTD model is performed using a lower concentration range of the experimental compound. Compounds 5 and 25 were well tolerated at 100, 200 and 300 mg/kg for 3 consecutive days of dosing. There were no adverse effects noted over the course of the study period.

Example 38

Dose Response Pharmacokinetic Parameters

Female BALB/c mice were given a dose of compounds 5 or 25 at 100, 200 and 300 mg kg' by oral gavage in a volume of 0.2 mL. At 2 and 4 hours after compound administration, animals were euthanized and cardiac blood (approximately 0.7 mL) was collected. Plasma was separated using centrifugation at 12,000 g for 20 min at 4° C. and stored at 80° C. Concentrations of compounds 5 and 25 in plasma were analyzed with LC-tandem MS (LC-MS/MS, AB SCIEX QTRAP 5500 system) with warfarin as internal standard. MS detection of mass transitions 295.2/135.2 (Compound 5), 299.2/146.1 (Compound 25) and 309.1/163.0 (Warfarin) was carried out. Concentration calculation was performed with MultiQuant Software (Version 2.1, AB SCIEX). The pharmacokinetic profile of the test compound was analyzed from plasma concentration-time data after oral administration.

Figure 2:
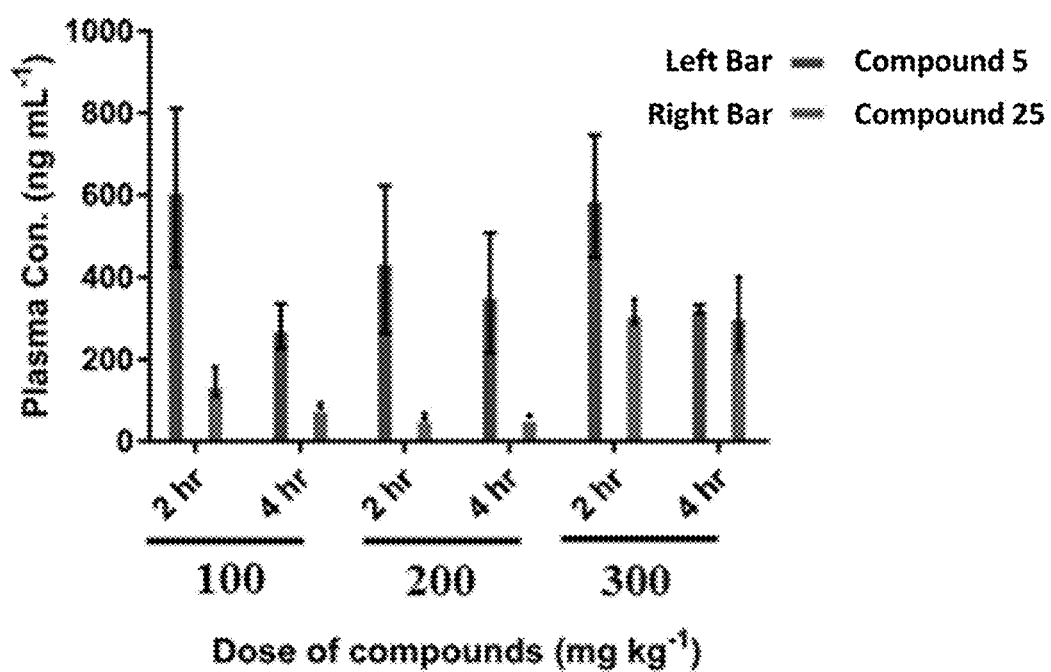
FIG. 2 shows in vivo dose response pharmacokinetic parameters of compounds 5 and 25. P.O. dosing at 100, 200 and 300 mg kg$^{-1}$ was administered; after administration, blood was collected at 2 and 4 hour time points for quantification. Plasma concentration of the compounds 5 and 25 was determined using liquid chromatography tandem mass spectrometry. Data are presented as mean±SD.

Comparative pharmacokinetic studies on the compounds 5 and 25 were carried out using liquid chromatography mass spectrometry (LC-MS) in order to determine the effective dose for the efficacy trial for growth inhibition of M. abscessus in vivo mouse model. A single dose of 100, 200 and 300 mg $kg^{-1}$ of compounds 5 or 25 was administered orally to female Blab/c mice. As shown in FIG. 2, compound 25 showed a lower blood concentration at 100 and 200 mg $kg^{-1}$ doses compared to compound 5, but it showed a similar concentration at a 300 mg $kg^{-1}$ dose compared to compound 5. This indicate the better PK profile of compounds 5 and 25 at 300 mg kg$^{-1}$. In view of these results, a dose of 300 mg kg$^{-1}$ was selected to carry out the efficacy studies described in Example 39.

Example 39

In Vivo Efficacy Assays 6-8 week old SCID female mice were ordered from Charles River. Mice were rested one week before infection. The acute SCID mouse model received an intravenous infection via the tail vein with 1×10$^6$ CFU/mouse (*M. abcessus* strain 103). Three mice were sacrificed day 1 post-infection to determine bacterial uptake. Whole lungs, spleens, and livers were extracted, homogenized in 4.5 mL of 1×PBS, and plated at (0-1-2-3-4-5-6-7) dilutions on 7H11 agar plates. The plates were placed in 37° C. dry-air incubator (strain dependent) for ~7 days. Compound 5 or 25 was administered by gavage in a volume of 100 µl per mouse which began day 2 post-infection and continued for 8 consecutive days. Compounds 5 and 25 were dosed at 300 mg/kg PO. In control mice, amikacin (AMI) was dosed at 150 mg/kg SQ injection in a volume of 100 µl per mouse per day.

Mice were sacrificed 2 days after administering the last dose of compounds 5 or 25. Six mice of all groups (untreated, control amikacin, and indolecarboxamides treated mice) were sacrificed and bacterial loads were determined by plating lung homogenate at 0-1-2-3-4-5-6-7, spleen at 0-1-2-3-4-5-6-7 and liver at 0-1-2-3-4-5-6-7. Log 10 protection values of at least 0.60 indicate activity was statistically significant. Statistical analysis was performed by first converting CFU to logarithms, which were then evaluated by a one-way ANOVA followed by a multiple comparison analysis of variance by a one-way Tukey test (SigmaStat software program). Differences were considered significant at the 95% level of confidence.

Antimicrobials: Amikacin was used as a positive, inter-experiment control and was purchased from Sigma (St. Louis, Mo.). Indolecarboxamides (compounds 5 and 25) were provided by Creighton University and diluted in an optimal formulation.

Intravenous Infection: Working stocks of *M. abcessus* strain 103 were frozen in 1 mL aliquots and stored at −80° C. before use. For infection, an aliquot was thawed, disrupted 20 times with a 1 mL luer-lok syringe fitted with a 26 gauge needle, and diluted in sterile 1×PBS. Female SCID mice, aged seven to nine weeks, were infected by intravenous infection with 1×10$^6$ CFU/mouse. Three mice were sacrificed day 1 post-infection to determine bacterial uptake. For this purpose, whole lungs, spleens, and livers were removed aseptically, homogenized in 4.5 mL of PBS and serial 1:10 dilutions (0-1-2-3-4-5-6-7) plated on 7H11/OADC agar plates. The plates were placed in a 37° C. dry-air incubator for ~7 days.

Antimicrobial Treatment: Treatment started 2 days post-infection (on day 2) and was continued for 8 consecutive days and given by gavage of compound 5 or 25 in vehicle in one dose determined by the formulation and MTD. The volume given was 100 µl per mouse once daily. The positive control was amikacin given SQ daily. All drugs were administered once daily.

Determination of Bacterial Load: To determine the bacterial loads on day 1, 3 mice were sacrificed to determine CFU counts in lungs, spleens, and livers. At the treatment start, untreated mice were sacrificed on the day of treatment initiation (day 2) to determine the pre-treatment CFU counts in lungs, spleens, and livers. Whole lungs, spleens, and livers were removed aseptically and homogenized in 4.5 mL sterile PBS. Homogenates were serially diluted in 1:10 dilutions and dilutions (0-1-2-3-4-5-6-7) plated on 7H11 agar plates.

Assessment of Treatment Efficacy: 1 day after the final treatment, mice were humanely euthanized by $CO_2$ asphyxiation, followed by cervical dislocation. Lung, spleen and liver were aseptically removed. Whole lungs, spleens and livers were homogenized in 4.5 mL sterile PBS, and diluted 1:10. Dilutions (0-1-2-3-4-5-6-7) were plated on 7H11 agar plates and incubated at 37° C. in a dry air incubator for 7 days.

Analysis of Efficacy Data: Lung, spleen and liver CFU numbers were log-transformed and evaluated by a one-way ANOVA followed by a multiple comparison analysis of variance by a one-way Tukey test (Graph pad software program). Differences were considered significant at the 95% level of confidence. All procedures involving animals were approved by the Colorado State University Animal Care and Use Committee.

Table 7 shows a summary of the treatment groups tested in the efficacy assays.

TABLE 7

| Treatment group | Compound | Dosing Regimen | Dosage (mg/kg) | Dosing Time or Interval | Sacrifice Time (days post infection) | n |
|---|---|---|---|---|---|---|
| 1 | untreated control | N/A | N/A | N/A | 1 | 3 |
| 2 | untreated control | N/A | N/A | N/A | 11 | 6 |
| 3 | Compound 5 + 20% cyclodextrin | gavage | 300 | 1x/daily | 11 | 12 |
| 5 | Compound 25 + 20% cyclodextrin | gavage | 300 | 1x/daily | 11 | 12 |
| 6 | amikacin (AMI) | SQ | 150 | 1x/daily | 11 | 12 |

Figures 3A, 3B, 3C:
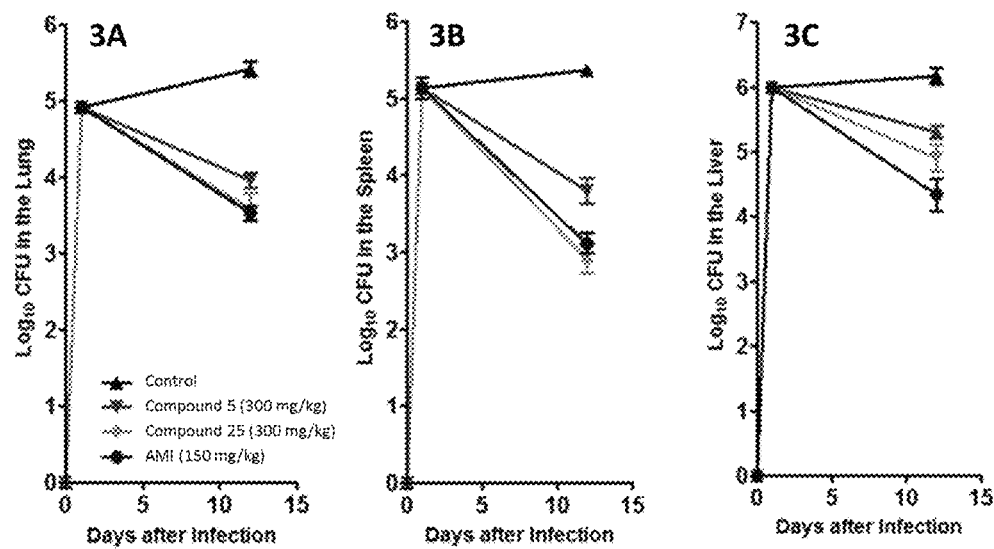
FIGS. 3A-3C shows results of an acute SCID nontuberculosis infection treatment mouse model. Bacterial counts in the lungs (A), spleens (B) and livers (C) of SCID mice intravenously infected with 1×10$^6$ CFUs of *M. abscessus* 103. The SCID mice were treated starting on day 2 for a total of 8 days with saline (▲), compound 5+20% cyclodextrin 300 mg/kg (▼), compound 25+20% cyclodextrin 300 mg/kg (♦), and amikacin (AMI) 150 mg/kg (●). Experimental groups of mice were evaluated for bacterial burden on day 1, 2 and 12 after infection by plating serial dilutions of organ homogenates on nutrient 7H11 agar and counting CFUs after 7 days incubation at 32° C. Results represent the average of one experiment (n=6 mice per experiment) bacterial load in each group is expressed as average Log$_{10}$ CFU (±SEM) cells (±SEM).

The results of lung, spleen, and liver CFU counts are shown in FIGS. 3A-3C. The mean lung, spleen and liver $log_{10}$ CFU at the start of drug treatment were 5.41±0.24, 5.41±0.15, and 6.17±0.33, respectively. Mice treated with daily doses of compound 5+20% cyclodextrin 300 mg/kg, or compound 25+20% cyclodextrin 300 mg/kg didn't demonstrate any significant weight loss in any of the groups and all animals survived until the Day 12 endpoint of the assay.

The $log_{10}$ CFU lung, spleen and liver counts on day 12 of the mice treated with the different drugs were as follows: AMI alone (3.52±0.22, 3.12±0.30, and 4.03±0.62, respectively) and compound 5+20% cyclodextrin 300 mg/kg (3.96±0.23, 3.79±0.40, and 5.30±0.23, respectively) and compound 25+20% cyclodextrin 300 mg/kg (3.58±0.50, 2.91±0.45 and 4.90±0.49, respectively).

The compound 5+20% cyclodextrin 300 mg/kg regimen resulted in CFU lung, spleen and liver counts that were approximately 3.96±0.23, 3.79±0.40, and 5.30±0.23 $\log_{10}$, respectively, which were higher than those in mice receiving AMI alone. The compound 25+20% cyclodextrin 300 mg/kg resulted in CFU lung, spleen and liver counts that were approximately 3.58±0.50, 2.91±0.45 and 4.90±0.49 $\log_{10}$, and showed lower CFU counts only in the spleen compared to those mice receiving AMI alone.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

What is claimed is:

1. A method of treating a non-tuberculosis mycobacterial infection in a subject in need thereof, comprising identifying the subject as having a non-tuberculosis mycobacterial infection, and administering to the subject a therapeutically effective amount of a compound
selected from the group consisting of:

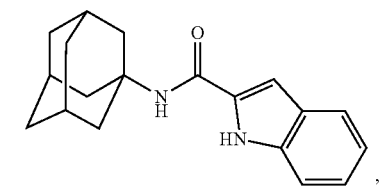

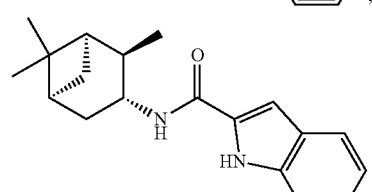

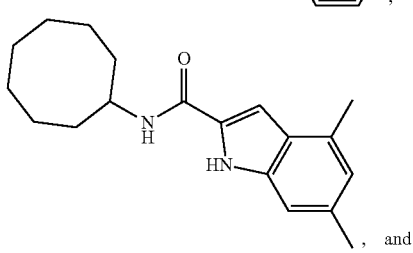

, and

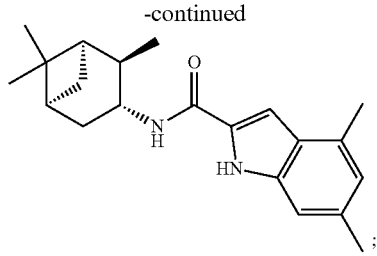

;

or a pharmaceutically acceptable salt thereof;
wherein the non-tuberculosis mycobacterium is selected from the group consisting of *M abscessus, M. massiliense, M. bolletii, M. chelonae*, and *M. avium*.

2. The method of claim 1, wherein the non-tuberculosis mycobacterial infection is a hospital acquired mycobacterial infection.

3. The method of claim 1, wherein the subject is further infected with a pathogen selected from *Pseudomonas aeruginosa* and *Staphylococcus aureus*, or a combination thereof.

4. The method of claim 1, wherein the subject has been identified as having a lung disease.

5. The method of claim 4, wherein the lung disease is selected from the group consisting of cystic fibrosis, bronchiectasis, emphysema, and chronic obstructive pulmonary disease, and bronchiectasis.

6. The method of claim 1, wherein the subject is a pediatric subject.

7. The method of claim 1, wherein the compound is selected from the group consisting of

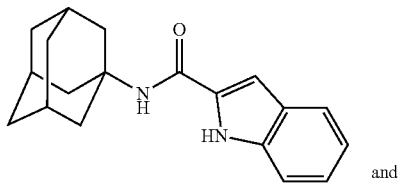

and

;

or a pharmaceutically acceptable salt thereof.

8. The method of claim 1, wherein the compound is:

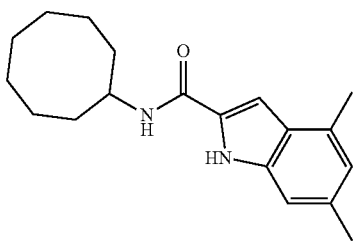 [SMILES: Cc1cc(C)c2cc(C(=O)NC3CCCCCCC3)[nH]c2c1]

or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 10,383,848 B2 |
| APPLICATION NO. | : 15/669289 |
| DATED | : August 20, 2019 |
| INVENTOR(S) | : North et al. |

Page 1 of 1

It is certified that error appears in the above-identified patent and that said Letters Patent is hereby corrected as shown below:

On the Title Page

Item (56), Column 2 (Other Publications), Line 34, Delete "Rifampinn.""  and insert -- Rifampin." --

Item (56), Column 2 (Other Publications), Line 49, Delete "Jemberg" and insert -- Jernberg --

In the Claims

Column 58, Line 13, Claim 1, delete "*M abscessus*" and insert -- *M. abscessus* --

Column 58, Line 27, Claim 5, delete ", and bronchiectasis"

Signed and Sealed this
Twenty-ninth Day of December, 2020

Andrei Iancu
*Director of the United States Patent and Trademark Office*